(12) United States Patent
Xu et al.

(10) Patent No.: US 8,048,889 B2
(45) Date of Patent: Nov. 1, 2011

(54) 3,4-DISUBSTITUTED COUMARIN AND QUINOLONE COMPOUNDS

(75) Inventors: Bin Xu, Wesley Hills, NY (US); Qiang Zhu, Piscataway, NJ (US); Hyun-Joon Cho, Spring Valley, NY (US); Reza Fathi, Hohokus, NJ (US); Zhen Yang, Ridgewood, NJ (US); Anthony Sandrasagra, Princeton, NJ (US); Yixin Liu, Paramus, NJ (US)

(73) Assignee: XTL Biopharmaceuticals Ltd. (IL)

( * ) Notice: Subject to any disclaimer, the term of this patent is extended or adjusted under 35 U.S.C. 154(b) by 1622 days.

(21) Appl. No.: 11/093,846

(22) Filed: Mar. 29, 2005

(65) Prior Publication Data

US 2006/0223783 A1  Oct. 5, 2006

(51) Int. Cl.
| | |
|---|---|
| *A61K 31/505* | (2006.01) |
| *A61K 31/35* | (2006.01) |
| *A61K 31/425* | (2006.01) |
| *A01N 43/54* | (2006.01) |
| *C07D 401/00* | (2006.01) |
| *C07D 239/02* | (2006.01) |
| *C07D 277/00* | (2006.01) |
| *C07D 311/02* | (2006.01) |

(52) U.S. Cl. ........ 514/275; 514/457; 514/256; 514/367; 514/365; 544/330; 544/331; 548/152; 549/283

(58) Field of Classification Search ................. 514/275, 514/256, 367, 365, 457; 544/330, 331; 548/152; 549/283

See application file for complete search history.

(56) References Cited

U.S. PATENT DOCUMENTS 5,430,153 A  7/1995  Pak et al.

FOREIGN PATENT DOCUMENTS

WO  WO 2005/068450 A1  7/2005

OTHER PUBLICATIONS

Checchi et al. "4-hydroxycoumarins. IX. Chlorination of 4-hydroxycoumarin and reactions of 4-chlorocoumarin with sodium derivative of esters and ketones containing an active methylene group," Gazzetta Chimica Italiana, 1969, vol. 95, No. 5, pp. 501-513. CA abstract, CN 1970:12491.*
International Search Report issued Nov. 22, 2006 in PCT/US2006/18857.
Karandashova, L.A. et al., "Basicity of 3-Formyl-4,7-Diaminocoumarins and Their Azomethine Derivatives," Chemistry of Heterocyclic Compounds, Mar. 1993, pp. 292-294, vol. 29, No. 3.
Kirpichenok, M.A. et al., "Reactions of 4-Chloro-7-Dialkylamino- and 3-Alkyl-4-Chloro-7-Dialkylaminocoumarins with Primary and Secondary Alkylamines," Chemistry of Heterocyclic Compounds, Jun. 1990, pp. 698-701, vol. 26, No. 26.
Kirpichenok, M.A. et al., "Synthesis and Spectral and Luminescent Properties of 3-Formyl-7-Dialkylaminocoumarins," Chemistry of Heterocyclic Compounds, Nov. 1991, pp. 1193-1199, vol. 27, No. 11.
Kuroki, Y., "Thermal Ene Reaction of 4-(2-Alkenylamino)-3-Formyl-2(2H)-Chromenones," Tetrahedron, 1994, pp. 1063-1072, vol. 50, No. 4.
Pryanishnikova, N.T. et al., "Synthesis and Study of the Pharmacological Properties of 3,4-Diaminocoumarins and 3-Substituted 4-Aminothiocoumarins," Pharmaceutical Chemistry Journal, 1978, pp. 1590-1593, vol. 12, No. 12.
Savel'Ev V.L. et al., "N-(3-Nitro(Amino)Coumarin-4-yl)Antrhranilic Acid Amines. Synthesis of 6, 7, 8, 13-Tetrahydro(1)Benzopyrano(4,3-b)(1,4)Benzodiazepine-6,8-Dione," Chemistry of Heterocyclic Compounds, Sep. 1989, pp. 1011-1014, vol. 25, No. 9.
Savel'Ev V.L. et al., "Synthesis and Pharmacological Activity of 4H-(1)-Benzopyrano(3,4-d)Imidazol-4-Ones," Pharmaceutical Chemistry Journal, Jun. 1983, pp. 423-425, vol. 17, No. 6.
Savel'Ev V.L. et al., "Synthesis and Study of the Properties of 4-Substituted 3-Aminomethylcoumarins," Chemistry of Heterocyclic Compounds, Jul. 1982, pp. 676-679, vol. 18, No. 7.
Stadlbauer, W. et al., "Isochinoline(4,3-c)chinolone aus Phenylmalonylheterocyclen," Monatshefte für Chemie, Jan. 1982, pp. 751-760, vol. 113. (English Summary on p. 2).
Stadlbauer, W. et al., "Synthese Von Indolen und Isochinolonen Aus Phenylmalonylheterocyclen/ / Synthesis of Indoles and Isoquinolones from Phenylmalonage Heterocycles," Monatshefte für Chemie, Springer Verlag, Jan. 1984, pp. 467-475, vol. 115, No. 4. (English Summary on p. 2).
Steinführer, T. et al., "Heterocyclisch (c)-anellierte Cumarine aus 4-Azido-3-cumarinecarbaldehyden," Liebigs Annalen der Chemie, 1992, pp. 23-28, vol. 1. (English Summary on p. 3).
Tabakovic, K. et al., "A Novel Transformation of 4-Arylaminocoumarins to 6H-1-Benzopyrano[4,3-b]quinolin-6-ones Under Vilsmeier-Haack Conditions," Synthesis, Mar. 1987, pp. 308-310, vol. 3.
Anschütz, R. "Über die Benzotetronsäuregruppe," Justus Liebigs Annalen der Chemie, 1909, pp. 219-270, vol. 367.
Bandyopadhyay, C. et al., "Synthesis of Coumarin Derivatives from 4-Oxo-4H-1-benzopyran-3-caroboxaldehyde via 3-(Arylaminomethylene)chromane-2,4-dione," Tetrahedon, 2000, pp. 3583-3587, vol. 56.
Bukalev, V.M. et al., "Synthesis of 4,7-Diamino-3-Formylcoumarins and Azomethines Derived from Them," Chemistry of Heterocyclic Compounds, Mar. 1993, pp. 282-291, vol. 29, No. 3.
Checchi, S. et al., "Ricerche Spora la 4-Idrossicumarina e Derivati—Nota IX Clorurazione Della 4-Idrossicumarina e Reazioni Fra 4-Clorocumarina e Composti Sodici Di Esteri e Chetoni Aventi Un Metilene Attivo," Gazzetta Chimica Italiana, Societa Chimica Italiana, 1969, pp. 501-513, vol. 99. (English Summary on p. 2).
European Extended Search Report, European Application No. 06759899.5, Jun. 8, 2010, 15 pages.
European Supplementary Search Report, European Application No. 06759899.5, Jun. 25, 2010, 1 page.
Heber, D., "2.5-Dioxo-2H,5H-(1)-benzopyrano(4,3-b)pyridine durch Cyclisierung 3-substituierter 4-Aminocumarine," Archiv der Pharmazie, Jul. 1987, pp. 577-581, vol. 320, No. 7. (English Summary on p. 3).
Ivanov, I.C. et al., "Two Methods for the Preparation of 3-Dialkylaminomethyl Derivatives (Mannich bases) of 4-Aminocoumarin: A New Type of Intramolecular Hydride Transfer," Synthesis, Jun. 1995, pp. 633-634, vol. 6.

\* cited by examiner

*Primary Examiner* — Shengjun Wang
(74) *Attorney, Agent, or Firm* — Fenwick & West LLP

(57) ABSTRACT

The present invention relates to 3,4-disubstituted coumarin and quinolone derivatives and processes for their preparation. The invention also related to methods for treating infection of Hepatitis C virus by administering a 3,4-disubstituted coumarin or quinolone derivative.

12 Claims, No Drawings

3,4-DISUBSTITUTED COUMARIN AND QUINOLONE COMPOUNDS

FIELD OF THE INVENTION

The present invention relates to 3,4-disubstituted coumarin and quinolone derivatives and processes for their preparation. The invention also related to methods for treating infection of Hepatitis C virus by administering a 3,4-disubstituted coumarin or quinolone derivative. The invention provides a synthetic process for the preparation of 3,4-disubstituted coumarin and quinolone derivatives using mild reaction conditions, which provides a high substituent tolerance and is appropriate for use in solid phase syntheses for producing a library of 3,4-disubstituted coumarin and quinolone derivatives for biological screening.

BACKGROUND OF THE INVENTION

Strategies in new drug discovery often look to natural products for leads in finding new chemical compounds with therapeutic properties. One of the recurring problems in drug discovery is the availability of organic compounds derived from natural sources. Techniques employing combinatorial chemistry attempt to overcome this problem by allowing the high throughput synthesis and testing of hundreds or thousands of related synthetic compounds, called a chemical library. In designing the synthesis of a prospective therapeutic compound or a chemical library, one often looks to natural chemical motifs which are known to have broad biological activity. Coumarin and Quinolone derivatives are of particular interest due to their frequent occurrence in nature and range of biological activities.

Coumarins are widely distributed in the plant kingdom. Approximately 50 naturally occurring coumarin derivatives have been identified. Derivatives of both coumarin and quinolone posses a range of biological activities. To avoid confusion, the coumarin and quinolone derivatives described herein are numbered according to the following convention:

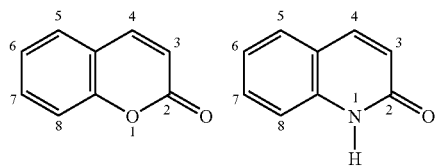

Infection with the Hepatitis C virus (HCV) represents a serious world-wide health crisis. In more than 70% of infected individuals, the virus evades clearance by the immune system leading to a persistent HCV infection. The long term effects of persistent HCV infection range from an apparently healthy carrier state to chronic hepatitis, liver fibrosis, cirrhosis, and eventually hepatocellular carcinoma. HCV is a leading cause of chronic liver disease. The best therapy currently available for treatment of HCV infection uses a combination of pegylated α-interferon and ribavirin. However, many of the patients treated with this therapy fail to show a sufficient antiviral response. Additionally, interferon treatment also induces severe side-effects (i.e. retinopathy, thyroiditis, acute pancreatitis, depression) that diminish the quality of life of treated patients. Thus, it is vital that more effective treatments be identified.

SUMMARY OF THE INVENTION

The present invention provides 3,4-disubstituted coumarin and quinolone derivatives having the formula I

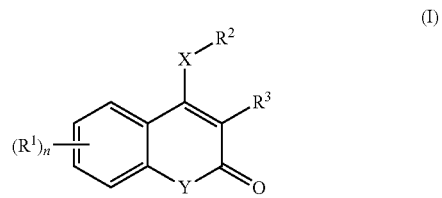

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from the group consisting of aralkyl, aryl, heteroaryl, cycloalkyl and cycloalkenyl;
$R^3$ is selected from the group consisting of alkyl, cycloalkyl, alkenyl, alkynyl, aralkyl, aryl, heteroaryl, —(CH$_2$)$_a$C(O)$R^{31}$, —(CH$_2$)$_a$C(O)N($R^{32}$)($R^{33}$), (CH$_2$)$_a$C(O)O$R^{31}$, —(CH$_2$)$_a$C(O)N($R^{32}$)($R^{33}$), —(CH$_2$)$_a$N($R^{32}$)($R^{33}$), —CH=N—$R^{34}$,
$R^{31}$ selected from H, alkyl, cycloalkyl, cycloalkenyl, alkenyl, alkynyl, aralkyl, aryl and heteroaryl;
$R^{32}$ and $R^{33}$ are independently selected from H, alkyl, cycloalkyl, cycloalkenyl, alkenyl, alkynyl, aralkyl, aryl and heteroaryl;
or $R^{32}$ and $R^{33}$ may be taken together with the nitrogen to which they are attached form a 5- to 7-membered ring which may optionally contain a further heteroatom;
$R^{34}$ is selected from alkyl, cycloalkyl, cycloalkenyl, alkenyl, alkynyl, aralkyl, aryl and heteroaryl
a is 0 to 6;
X is selected from O and N—$R^4$;
$R^4$ is selected from the group consisting of H, alkyl, cycloalkyl, alkenyl, alkynyl, aralkyl, aryl, heteroaryl, —(CH$_2$)$_b$C(O)$R^{41}$, —(CH$_2$)$_b$C(O)N($R^{42}$)($R^{43}$), —(CH$_2$)$_b$C(O)O$R^{41}$, and —(CH$_2$)$_b$C(O)N($R^{42}$)($R^{43}$),
each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

Y is selected from O and N—$R^5$;

$R^5$ is selected from the group consisting of H, alkyl, cycloalkyl, alkenyl, alkynyl, aralkyl, aryl, heteroaryl, —(CH$_2$)$_b$C(O)R$^{51}$, —(CH$_2$)$_b$C(O)N(R$^{52}$)(R$^{53}$), and —(CH$_2$)$_b$C(O)OR$^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom; and b is 0 to 6;

or a pharmaceutically acceptable salt or hydrate thereof.

The invention also provides a synthetic process for the preparation of compounds of the formula I. The process uses mild reaction conditions, which provides a high substituent tolerance. Thus, the process is applicable to the preparation of a wide variety of 3,4-disubstituted coumarin and quinolone derivatives with diverse substitution patterns. Additionally, the process is appropriate for use with combinatorial synthesis techniques. Thus, the process provides a method for producing a library of 3,4-disubstituted coumarin and quinolone derivatives for biological screening.

The invention also provides compositions and methods for the treatment of HCV by administering a compound of the present invention in a therapeutically effective amount.

DETAILED DESCRIPTION OF THE INVENTION

The term "halo" or "halogen" as used herein includes fluorine, chlorine, bromine and iodine.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl, and the like. The alkyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, cycloalkyl, cycloalkenyl, aryl and heteroaryl.

The term "alkenyl" as used herein contemplates substituted or unsubstituted, straight and branched chain alkene radicals containing from two to 8 carbon atoms. The alkenyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, cycloalkyl, cycloalkenyl, aryl and heteroaryl.

The term "alkynyl" as used herein contemplates substituted or unsubstituted, straight and branched carbon chain containing from two to 8 carbon atoms and having at least one carbon-carbon triple bond. The term alkynyl includes, for example ethynyl, 1-propynyl, 2-propynyl, 1-butynyl, 3-methyl-1-butynyl, and the like. The alkynyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, cycloalkyl, cycloalkenyl, aryl and heteroaryl.

The term "cycloalkyl" as used herein contemplates substituted or unsubstituted cyclic alkyl radicals containing form 3 to 7 carbon atoms and includes cyclopropyl, cyclopentyl, cyclohexyl, and the like. The cycloalkyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, alkyl, cycloalkenyl, aryl and heteroaryl.

The term "cycloalkenyl" as used herein contemplates substituted or unsubstituted cyclic alkenyl radicals containing form 5 to 7 carbon atoms in which has a double bond between two of the ring carbons and includes cyclopentenyl, cyclohexenyl, and the like. The cycloalkenyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, alkyl, cycloalkenyl, aryl and heteroaryl.

The term "aralkyl" as used herein contemplates a lower alkyl group which has as a substituent an aromatic group, which aromatic group may be substituted or unsubstituted. The aralkyl group may be optionally substituted with one or more substituents selected from halo, CN, NO$_2$, CO$_2$R, C(O)R, —O—R, —N(R')(R''), —N(R)C(O)R, —N(R)SO$_2$R, —SR, —C(O)N(R')(R''), —OC(O)R, —OC(O)N(R')(R''), SO$_2$, —SOR, —SO$_3$R, —SO$_2$N(R')(R''), phosphate, phosphonate, cycloalkyl, cycloalkenyl, aryl and heteroaryl.

The terms phosphate and phosphonate as used herein refer to the moieties having the following structures, respectively:

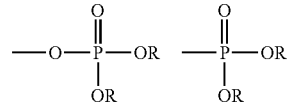

The term "heterocyclic group" or "heterocyclic ring" as used herein contemplates substituted or unsubstituted aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. The heterocyclic group may be optionally substituted with one or more substituents selected from halo, alkyl, CN, $NO_2$, $CO_2R$, $C(O)R$, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2$N(R')(R"), phosphate, phosphonate, cycloalkyl, cycloalkenyl, aryl and heteroaryl.

The terms "aryl", "aromatic group", or "aromatic ring" as used herein contemplates substituted or unsubstituted single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halo, alkyl, CN, $NO_2$, $CO_2R$, $C(O)R$, —O—R, —N(R')(R"), —N(R)C(O)R, —N(R)$SO_2R$, —SR, —C(O)N(R')(R"), —OC(O)R, —OC(O)N(R')(R"), $SO_2$, —SOR, —$SO_3R$, —$SO_2$N(R')(R"), phosphate, phosphonate, cycloalkyl, cycloalkenyl, aryl and heteroaryl.

Each R is independently selected from H, alkyl, cycloalkyl, cycloalkenyl, alkenyl, alkynyl, aralkyl, aryl and heteroaryl. Each R' and R" are independently selected from H, alkyl, cycloalkyl, cycloalkenyl, alkenyl, alkynyl, aralkyl, aryl and heteroaryl; or R' and R" may be taken together with the nitrogen to which they are attached form a 5- to 7-membered ring which may optionally contain a further heteroatom.

The term "heteroatom", particularly as a ring heteroatom, refers to N, O, and S.

All value ranges, for example those given for n and m, are inclusive over the entire range. Thus, a range of 0 to 4 would include the values 0, 1, 2, 3 and 4.

The present invention provides compounds of the formula I:

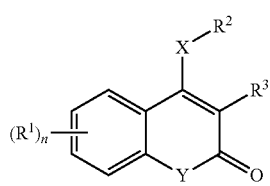

(I)

wherein:
each $R^1$ is independently selected from alkyl, alkenyl, alkynyl, aralkyl, —O—$R^{11}$, —N($R^{12}$)($R^{13}$), —N($R^{13}$)C(O)R, —N($R^{11}$)$SO_2R^{11}$, —$SR^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, $CF_3$, $NO_2$, $SO_2$, —$SOR^{11}$, —$SO_3R^{11}$, —$SO_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from the group consisting of aralkyl, aryl, heteroaryl, cycloalkyl and cycloalkenyl;
$R^3$ is selected from the group consisting of alkyl, cycloalkyl, alkenyl, alkynyl, aralkyl, aryl, heteroaryl, —$(CH_2)_aC(O)R^{31}$, —$(CH_2)_aC(O)N(R^{32})(R^{33})$, $(CH_2)_aC(O)OR^{31}$, —$(CH_2)_aC(O)N(R^{32})(R^{33})$, —$(CH_2)_aN(R^{32})(R^{33})$, —CH=N—$R^{34}$,
$R^{31}$ selected from H, alkyl, cycloalkyl, cycloalkenyl, alkenyl, alkynyl, aralkyl, aryl and heteroaryl;
$R^{32}$ and $R^{33}$ are independently selected from H, alkyl, cycloalkyl, cycloalkenyl, alkenyl, alkynyl, aralkyl, aryl and heteroaryl;
or $R^{32}$ and $R^{33}$ may be taken together with the nitrogen to which they are attached form a 5- to 7-membered ring which may optionally contain a further heteroatom;
$R^{34}$ is selected from alkyl, cycloalkyl, cycloalkenyl, alkenyl, alkynyl, aralkyl, aryl and heteroaryl
a is 0 to 6;
X is selected from O and N—$R^4$;
$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$,
each $R^{41}$ is independently selected from H, alkyl, cycloalkyl, cycloalkenyl, alkenyl, alkynyl, aralkyl, aryl and heteroaryl;
$R^{42}$ and $R^{43}$ are independently selected from H, alkyl, cycloalkyl, cycloalkenyl, alkenyl, alkynyl, aralkyl, aryl and heteroaryl;
or $R^{42}$ and $R^{43}$ may be taken together with the nitrogen to which they are attached form a 5- to 7-membered ring which may optionally contain a further heteroatom;
b is 0 to 6;
Y is selected from O and N—$R^5$;
$R^5$ is selected from the group consisting of H, alkyl, cycloalkyl, alkenyl, alkynyl, aralkyl, aryl, heteroaryl, —$(CH_2)_bC(O)R^5$, —$(CH_2)_bC(O)N(R^{52})(R^{53})$, and —$(CH_2)_bC(O)OR^{51}$;
each $R^{51}$ is independently selected from H, alkyl, cycloalkyl, cycloalkenyl, alkenyl, alkynyl, aralkyl, aryl and heteroaryl;
$R^{52}$ and $R^{53}$ are independently selected from H, alkyl, cycloalkyl, cycloalkenyl, alkenyl, alkynyl, aralkyl, aryl and heteroaryl;
or $R^{52}$ and $R^{53}$ may be taken together with the nitrogen to which they are attached form a 5- to 7-membered ring which may optionally contain a further heteroatom; and
b is 0 to 6;
or a pharmaceutically acceptable salt or hydrate thereof.

The substances according to the invention may be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

In preferred embodiments of the invention, $R^2$ is selected from aryl and aralkyl.

In one embodiment of the invention, Y is selected to be a O to give a compound of the formula II:

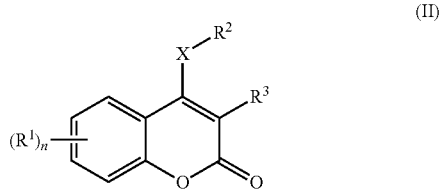

(II)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;
or $R^{12}$ and $R^{13}$ may be taken together with the nitrogen to which they are attached form a 5- to 7-membered ring which may optionally contain a further heteroatom, n is 0 to 4;
$R^2$ is selected from the group consisting of aralkyl, aryl, heteroaryl, cycloalkyl and cycloalkenyl;
$R^3$ is selected from the group consisting of alkyl, cycloalkyl, alkenyl, alkynyl, aralkyl, aryl, heteroaryl, —(CH$_2$)$_a$C(O)$R^{31}$, —(CH$_2$)$_a$C(O)N($R^{32}$)($R^{33}$), (CH$_2$)$_a$C(O)O$R^{31}$, —(CH$_2$)$_a$C(O)N($R^{32}$)($R^{33}$), —(CH$_2$)$_a$N($R^{32}$)($R^{33}$), —CH=N—$R^{34}$,
$R^{31}$ selected from H, alkyl, cycloalkyl, cycloalkenyl, alkenyl, alkynyl, aralkyl, aryl and heteroaryl;
$R^{32}$ and $R^{33}$ are independently selected from H, alkyl, cycloalkyl, cycloalkenyl, alkenyl, alkynyl, aralkyl, aryl and heteroaryl;
or $R^{32}$ and $R^{33}$ may be taken together with the nitrogen to which they are attached form a 5- to 7-membered ring which may optionally contain a further heteroatom;
$R^{34}$ is selected from alkyl, cycloalkyl, cycloalkenyl, alkenyl, alkynyl, aralkyl, aryl and heteroaryl;
a is 0 to 6;
X is selected from O and N—$R^4$;
$R^4$ is selected from the group consisting of H, alkyl, cycloalkyl, alkenyl, alkynyl, aralkyl, aryl, heteroaryl, —(CH$_2$)$_b$C(O)$R^{41}$, —(CH$_2$)$_b$C(O)N($R^{42}$)($R^{43}$), —(CH$_2$)$_b$C(O)O$R^{41}$, and —(CH$_2$)$_b$C(O)N($R^{42}$)($R^{43}$),
each $R^{41}$ is independently selected from H, alkyl, cycloalkyl, cycloalkenyl, alkenyl, alkynyl, aralkyl, aryl and heteroaryl;
$R^{42}$ and $R^{43}$ are independently selected from H, alkyl, cycloalkyl, cycloalkenyl, alkenyl, alkynyl, aralkyl, aryl and heteroaryl;
or $R^{42}$ and $R^{43}$ may be taken together with the nitrogen to which they are attached form a 5- to 7-membered ring which may optionally contain a further heteroatom; and
b is 0 to 6;
or a pharmaceutically acceptable salt or hydrate thereof.

In a further embodiment of the invention, X of a compound according to formula II is selected to be a O to give a compound of the formula III:

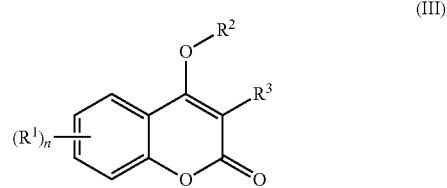

(III)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N(R)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^2$ is selected from the group consisting of aralkyl, aryl, heteroaryl, cycloalkyl and cycloalkenyl;

$R^3$ is selected from the group consisting of alkyl, cycloalkyl, alkenyl, alkynyl, aralkyl, aryl, heteroaryl, —$(CH_2)_aC(O)R^{31}$, —$(CH_2)_aC(O)N(R^{32})(R^{33})$, $(CH_2)_aC(O)OR^{31}$, —$(CH_2)_aC(O)N(R^{32})(R^{33})$, —$(CH_2)_aN(R^{32})(R^{33})$, —CH=N—$R^{34}$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

$R^{34}$ is selected from alkyl, cycloalkyl, cycloalkenyl, alkenyl, alkynyl, aralkyl, aryl and heteroaryl; and a is 0 to 6;

or a pharmaceutically acceptable salt or hydrate thereof.

In further preferred embodiment of the invention, $R^2$ and $R^3$ of a compound according to formula III are selected to be a —$CH_2$—$R^6$ and —$CH_2$—$R^7$, respectively, to give a compound of the formula IV:

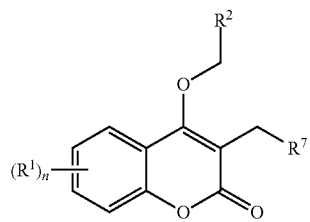

(IV)

wherein:

each $R^1$ is independently selected from alkyl, alkenyl, alkynyl, aralkyl, —$OR^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^6$ is selected from the group consisting of aryl and heteroaryl;

$R^7$ is selected from the group consisting of aryl, heteroaryl, —$C(O)R^{31}$, —$C(O)N(R^{32})(R^{33})$, —$C(O)OR^{31}$, —$C(O)N(R^{32})(R^{33})$, and —$N(R^{32})(R^{33})$, $R^{31}$ selected from H, alkyl, cycloalkyl, cycloalkenyl, alkenyl, alkynyl, aralkyl, aryl and heteroaryl; and $R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

or a pharmaceutically acceptable salt or hydrate thereof.

In a preferred embodiment for compounds of the formula IV, $R^7$ is selected to be an aryl or heteroaryl groups.

In another embodiment of the invention, $R^2$ of a compound according to formula III is selected to be a benzyl group to give a compound of the formula V:

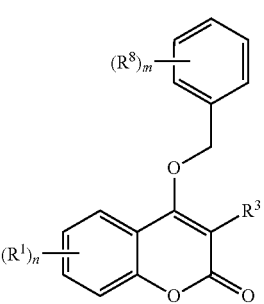

(V)

wherein:

each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, halo, phosphate, phosphonate, aryl and heteroaryl;

additionally or alternatively two RI substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^3$ is selected from the group consisting of alkyl, cycloalkyl, alkenyl, alkynyl, aralkyl, aryl, heteroaryl, —$(CH_2)_aC(O)R^{31}$, —$(CH_2)_aC(O)N(R^{32})(R^{33})$, $(CH_2)_aC(O)OR^{31}$, —$(CH_2)_aC(O)N(R^{32})(R^{33})$, $(CH_2)_aN(R^{32})(R^{33})$, —CH=N—$R^{34}$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

$R^{34}$ is selected from alkyl, cycloalkyl, cycloalkenyl, alkenyl, alkynyl, aralkyl, aryl and heteroaryl a is 0 to 6;

each $R^8$ is independently selected from the group consisting of halo, alkyl, CN, $NO_2$, $CO_2R^{81}$, $C(O)R^{81}$, —O—$R^{81}$, —$N(R^{82})(R^{83})$, —$N(R^{81})C(O)R^{81}$, —$N(R^{81})SO_2R^{81}$, —$SR^{81}$, —$C(O)N(R^{82})(R^{83})$, —$OC(O)R^{81}$, —$OC(O)N(R^{82'})(R^{83})$, $SO_2$, —$SOR^{81}$, —$SO_3R^{81}$, —$SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom; and m is 0 to 5;

or a pharmaceutically acceptable salt or hydrate thereof.

In further preferred embodiment of the invention, $R^6$ and $R^7$ of a compound according to formula IV are selected to be phenyl groups, to give a compound of the formula VI:

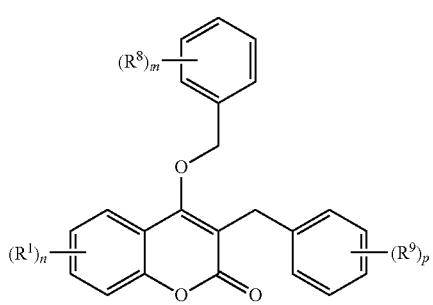

(VI)

wherein:

each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

each $R^8$ is independently selected from the group consisting of halo, alkyl, CN, $NO_2$, $CO_2R^{81}$, $C(O)R^{81}$, —O—$R^{81}$, —$N(R^{82})(R^{83})$, —$N(R^{81})C(O)R$ , —$N(R^{81})SO_2R^{81}$, —$SR^{81}$, —$C(O)N(R^{82})(R^{83})$, —$OC(O)R^{81}$, —$OC(O)N(R^{82'})(R^{83})$, $SO_2$, —$SOR^{81}$, —$SO_3R^{81}$, —$SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom;

m is 0 to 5;

each $R^9$ is independently selected from the group consisting of halo, alkyl, CN, $NO_2$, $CO_2R^{91}$, $C(O)R^{91}$, —O—$R^{91}$, —$N(R^{92})(R^{93})$, —$N(R^{91})C(O)R^{91}$, —$N(R^{91})SO_2R^{91}$, —$SR^{91}$, —$C(O)N(R^{92})(R^{93})$, —$OC(O)R^{91}$, —$OC(O)N(R^{92})(R^{93})$, $SO_2$, —$SOR^{91}$, —$SO_3R^{91}$, —$SO_2N(R^{92})(R^{93})$, cycloalkyl, cycloalkenyl, aryl and heteroaryl;

each $R^{91}$ is independently selected from H, alkyl, cycloalkyl, cycloalkenyl, alkenyl, alkynyl, aralkyl, aryl and heteroaryl;

each $R^{92}$ and $R^{93}$ are independently selected from H, alkyl, cycloalkyl, cycloalkenyl, alkenyl, alkynyl, aralkyl, aryl and heteroaryl; or $R^{92}$ and $R^{93}$ may be taken together with the nitrogen to which they are attached form a 5- to 7-membered ring which may optionally contain a further heteroatom; and p is 0 to 5;

or a pharmaceutically acceptable salt or hydrate thereof.

Exemplary compounds of the formula VI include the following structures:

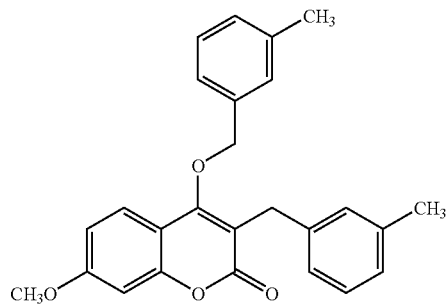

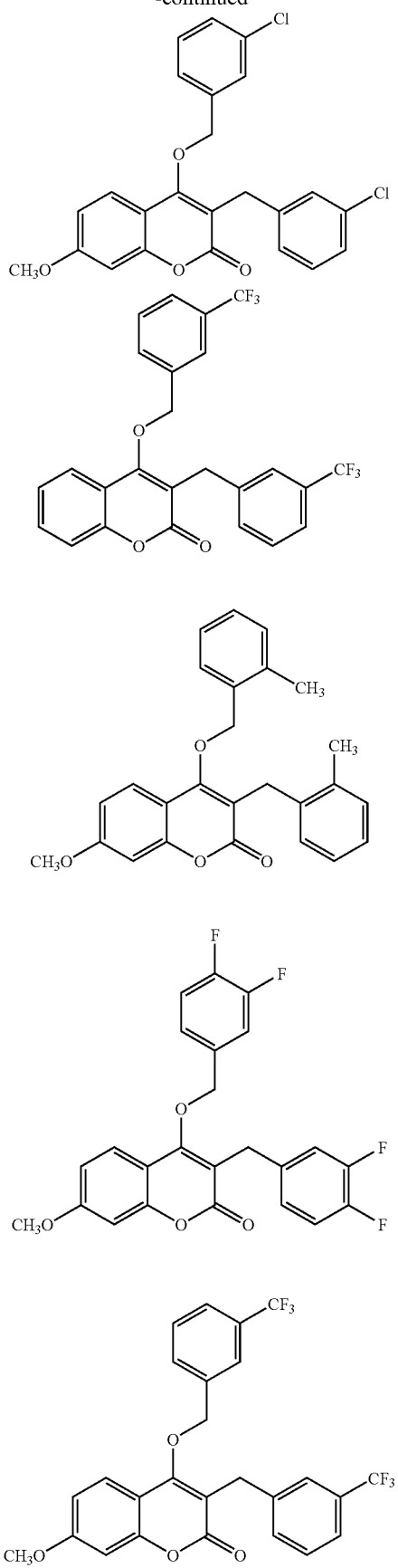

-continued

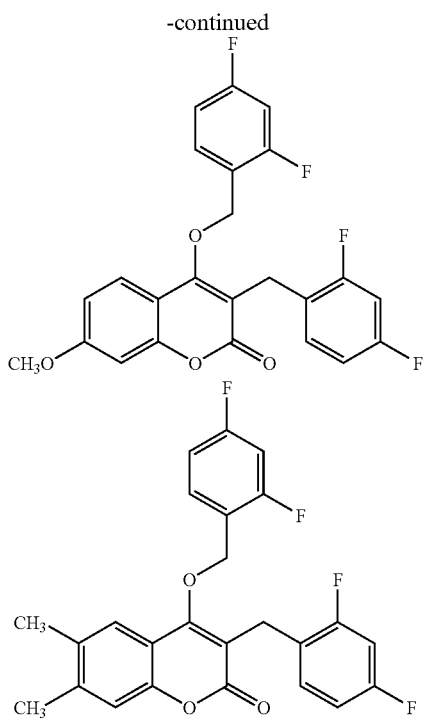

In a another embodiment of the invention, X of a compound according to formula II is selected to be a N—R$^4$ to give a compound of the formula VII:

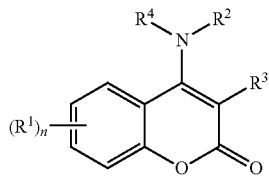

(VII)

wherein:
each R$^1$ is independently selected from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O—R$^{11}$, cycloalkyl, cycloalkenyl, halo, phosphate, phosphonate, aryl and heteroaryl;
additionally or alternatively two R$^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from R$^1$;
each R$^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and heteroaryl; or R$^{12}$ and R$^{13}$ may be taken together with the nitrogen to which they are attached form a 5- to 7-membered ring which may optionally contain a further heteroatom,
n is 0 to 4;
R$^2$ is selected from the group consisting of aralkyl, aryl, heteroaryl, cycloalkyl and cycloalkenyl;
R$^3$ is selected from the group consisting of alkyl, cycloalkyl, alkenyl, alkynyl, aralkyl, aryl, heteroaryl, —(CH$_2$)$_a$C(O)R$^{31}$, —(CH$_2$)$_a$C(O)N(R$^{32}$)(R$^{33}$), —(CH$_2$)$_a$C(O)OR$^{31}$, —(CH$_2$)$_a$C(O)N(R$^{32}$)(R$^{33}$), —(CH$_2$)$_a$N(R$^{32}$)(R$^{33}$), —CH═N—R$^{34}$,
R$^{31}$ selected from H, alkyl, cycloalkyl, cycloalkenyl, alkenyl, alkynyl, aralkyl, aryl and heteroaryl;
R$^{32}$ and R$^{33}$ are independently selected from H, alkyl, cycloalkyl, cycloalkenyl, alkenyl, alkynyl, aralkyl, aryl and heteroaryl;
or R$^{32}$ and R$^{33}$ may be taken together with the nitrogen to which they are attached form a 5- to 7-membered ring which may optionally contain a further heteroatom;
R$^{34}$ is selected from alkyl, cycloalkyl, cycloalkenyl, alkenyl, alkynyl, aralkyl, aryl and heteroaryl
a is 0 to 6;
R$^4$ is selected from the group consisting of H, alkyl, cycloalkyl, alkenyl, alkynyl, aralkyl, aryl, heteroaryl, —(CH$_2$)$_b$C(O)R$^{41}$, —(CH$_2$)$_b$C(O)N(R$^{42}$)(R$^{43}$), —(CH$_2$)$_b$C(O)OR$^{41}$, and —(CH$_2$)$_b$C(O)N(R$^{42}$)(R$^{43}$),
each R$^{41}$ is independently selected from H, alkyl, cycloalkyl, cycloalkenyl, alkenyl, alkynyl, aralkyl, aryl and heteroaryl;
R$^{42}$ and R$^{43}$ are independently selected from H, alkyl, cycloalkyl, cycloalkenyl, alkenyl, alkynyl, aralkyl, aryl and heteroaryl;
or R$^{42}$ and R$^{43}$ may be taken together with the nitrogen to which they are attached form a 5- to 7-membered ring which may optionally contain a further heteroatom; and
b is 0 to 6;
or a pharmaceutically acceptable salt or hydrate thereof.

In a preferred embodiment for compounds of the formula VII, R3 is selected to be —CH═N—R$^{34}$, to give a compound of the formula VII$_a$

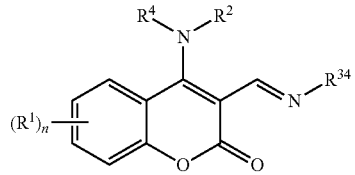

wherein:
each R$^1$ is independently selected from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O—R$^{11}$, cycloalkyl, cycloalkenyl, halo, phosphate, phosphonate, aryl and heteroaryl;
additionally or alternatively two R$^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from R$^1$;
each R$^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each R$^{12}$ and R$^{13}$ are independently selected from H, alkyl, cycloalkyl, cycloalkenyl, alkyl-O-alkyl, alkyl- O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from the group consisting of aralkyl, aryl, heteroaryl, cycloalkyl and cycloalkenyl;

$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6; and $R^{34}$ is selected from alkyl, cycloalkyl, cycloalkenyl, alkenyl, alkynyl, aralkyl, aryl and heteroaryl;

or a pharmaceutically acceptable salt or hydrate thereof.

In a preferred embodiment for compounds of the formula VII and VII$_a$, $R^2$ is selected to be an aryl or heteroaryl groups. I further preferred embodiments, $R^4$ is H.

Exemplary compounds of the formula VII$_a$ include the following structures:

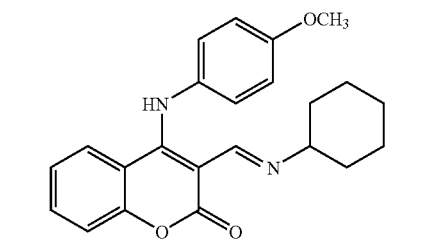

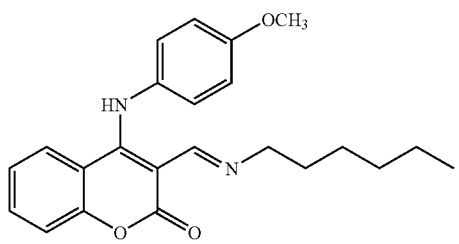

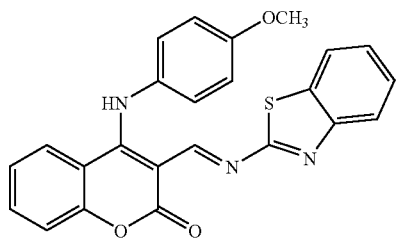

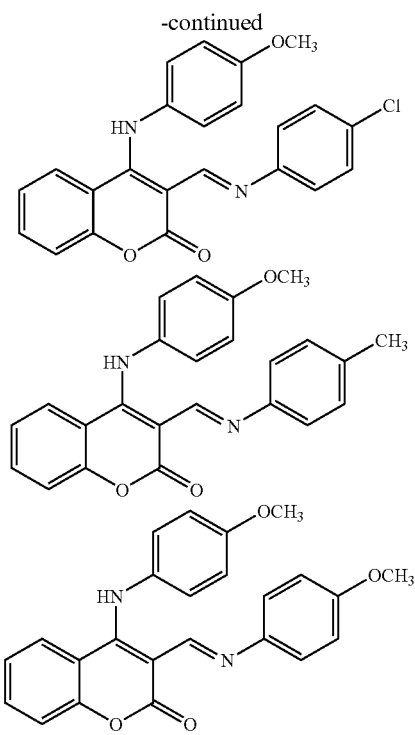

In further preferred embodiment of the invention, $R^2$ and $R^3$ of a compound according to formula VII are selected to be a —$CH_2$—$R^6$ and —$CH_2$—$R^7$, respectively, to give a compound of the formula VIII:

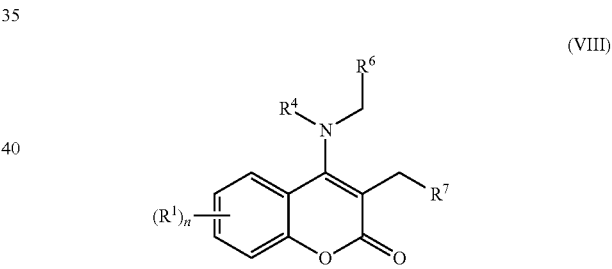

(VIII)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

$R^6$ is selected from the group consisting of aryl and heteroaryl;

$R^7$ is selected from the group consisting of aryl, heteroaryl, —$C(O)R^{31}$, —$C(O)N(R^{32})(R^{33})$, —$C(O)OR^{31}$, —$C(O)N(R^{32})(R^{33})$, and —$N(R^{32})(R^{33})$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

or a pharmaceutically acceptable salt or hydrate thereof.

In a preferred embodiment for compounds of the formula VIII, $R^7$ is selected to be an aryl or heteroaryl groups.

In another embodiment of the invention, $R^2$ of a compound according to formula VII is selected to be a benzyl group to give a compound of the formula IX:

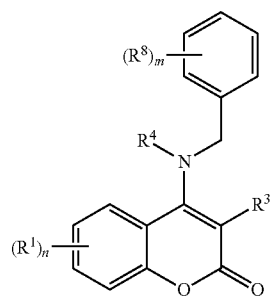

(IX)

wherein:

each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, phosphate, phosphonate, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^3$ is selected from the group consisting of alkyl, cycloalkyl, alkenyl, alkynyl, aralkyl, aryl, heteroaryl, —$(CH_2)_aC(O)R^{31}$, —$(CH_2)_aC(O)N(R^{32})(R^{33})$, $(CH_2)_aC(O)OR^{31}$, —$(CH_2)_aC(O)N(R^{32})(R^{33})$, —$(CH_2)_aN(R^{32})(R^{33})$, —CH=N—$R^{34}$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

$R^{34}$ is selected from alkyl, cycloalkyl, cycloalkenyl, alkenyl, alkynyl, aralkyl, aryl and heteroaryl a is 0 to 6;

$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, $NO_2$, $CO_2R^{81}$, $C(O)R^8$, —O—$R^{81}$, —$N(R^{82})(R^{83})$, —$N(R^{81})C(O)R^{81}$, —$N(R^{81})SO_2R^{81}$, —$SR^{81}$, —$C(O)N(R^{82})(R^{83})$, —$OC(O)R^{81}$, —$OC(O)N(R^{82})(R^{83})$, $SO_2$, —$SOR^{81}$, —$SO_3R$, —$SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom; and m is 0 to 5;

or a pharmaceutically acceptable salt or hydrate thereof.

In further preferred embodiment of the invention, $R^6$ and $R^7$ of a compound according to formula VIII are selected to be phenyl groups, to give a compound of the formula X:

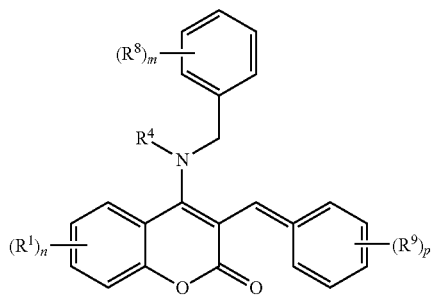

(X)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, phosphate, phosphonate, halo, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^4$ is selected from the group consisting of H, alkyl, cycloalkyl, alkenyl, alkynyl, aralkyl, aryl, heteroaryl, —(CH$_2$)$_b$C(O)$R^{41}$, —(CH$_2$)$_b$C(O)N($R^{42}$)($R^{43}$), —(CH$_2$)$_b$C(O)O$R^{41}$, and —(CH$_2$)$_b$C(O)N($R^{42}$)($R^{43}$), each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, NO$_2$, CO$_2$$R^{81}$, C(O)$R^{81}$, —O—$R^{81}$, —N($R^{82}$)($R^{83}$), —N($R^{81}$)C(O)$R^{81}$, —N($R^{81}$)SO$_2$$R^{81}$, —S$R^{81}$, —C(O)N($R^{82}$)($R^{83}$), —OC(O)$R^{81}$, —OC(O)N($R^{82}$)($R^{83}$), SO$_2$, —SO$R^{81}$, —SO$_3$$R^{81}$, —SO$_2$N($R^{82}$)($R^{83}$), cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom;

m is 0 to 5;

each $R^9$ is independently selected from the group consisting of halo, alkyl, CN, NO$_2$, CO$_2$$R^{91}$, C(O)$R^{91}$, —O—$R^{91}$, —N($R^{92}$)($R^{93}$), —N($R^{91}$)C(O)$R^{91}$, —N($R^{91}$)SO$_2$$R^{91}$, —S$R^{91}$, —C(O)N($R^{92}$)($R^{93}$), —OC(O)$R^{91}$, —OC(O)N($R^{92}$)($R^{93}$), SO$_2$, —SO$R^{91}$, —SO$_3$$R^{91}$, —SO$_2$N($R^{92}$)($R^{93}$), cycloalkyl, cycloalkenyl, aryl and heteroaryl;

each $R^{91}$ is independently selected from H, alkyl, cycloalkyl, cycloalkenyl, alkenyl, alkynyl, aralkyl, aryl and heteroaryl;

each $R^{92}$ and $R^{93}$ are independently selected from H, alkyl, cycloalkyl, cycloalkenyl, alkenyl, alkynyl, aralkyl, aryl and heteroaryl; or $R^{92}$ and $R^{93}$ may be taken together with the nitrogen to which they are attached form a 5- to 7-membered ring which may optionally contain a further heteroatom; and p is 0 to 5;

or a pharmaceutically acceptable salt or hydrate thereof.

In another embodiment of the invention, Y is selected to be a N—$R^5$ to give a compound of the formula XI:

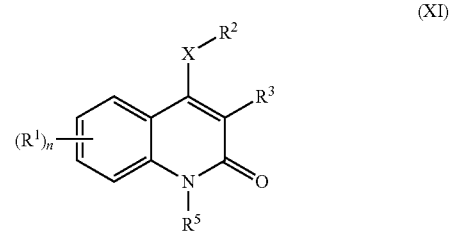

(XI)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2$$R^{11}$, —S$R^{11}$, —C(O)$R^{11}$, —C(O)O$R^{11}$, —C(O)N($R^{12}$)($R^{11}$), —OC(O)$R^{11}$, —OC(O)N($R^{12}$)($R^{13}$), CN, CF$_3$, NO$_2$, SO$_2$, —SO$R^{11}$, —SO$_3$$R^{11}$, —SO$_2$N($R^{12}$)($R^{13}$), -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^2$ is selected from the group consisting of aralkyl, aryl, heteroaryl, cycloalkyl and cycloalkenyl;

$R^3$ is selected from the group consisting of alkyl, cycloalkyl, alkenyl, alkynyl, aralkyl, aryl, heteroaryl, —(CH$_2$)$_a$C(O)$R^{31}$, —(CH$_2$)$_a$C(O)N($R^{32}$)($R^{33}$), (CH$_2$)$_a$C(O)O$R^{31}$, —(CH$_2$)$_a$C(O)N($R^{32}$)($R^{33}$), —(CH$_2$)$_a$N($R^{32}$)($R^{33}$), —CH=N—$R^{34}$, R$^{31}$ selected from H, alkyl, cycloalkyl, cycloalkenyl, alkenyl, alkynyl, aralkyl, aryl and heteroaryl;

R$^{32}$ and R$^{33}$ are independently selected from H, alkyl, cycloalkyl, cycloalkenyl, alkenyl, alkynyl, aralkyl, aryl and heteroaryl;

or R$^{32}$ and R$^{33}$ may be taken together with the nitrogen to which they are attached form a 5- to 7-membered ring which may optionally contain a further heteroatom;

R$^{34}$ is selected from alkyl, cycloalkyl, cycloalkenyl, alkenyl, alkynyl, aralkyl, aryl and heteroaryl a is 0 to 6;

X is selected from O and N—R$^4$;

R$^4$ is selected from the group consisting of H, alkyl, cycloalkyl, alkenyl, alkynyl, aralkyl, aryl, heteroaryl, —(CH$_2$)$_b$C(O)R$^{41}$, —(CH$_2$)$_b$C(O)N(R$^{42}$)(R$^{43}$), —(CH$_2$)$_b$C(O)OR$^{41}$, and —(CH$_2$)$_b$C(O)N(R$^{42}$)(R$^{43}$), each R$^{41}$ is independently selected from H, alkyl, cycloalkyl, cycloalkenyl, alkenyl, alkynyl, aralkyl, aryl and heteroaryl;

R$^{42}$ and R$^{43}$ are independently selected from H, alkyl, cycloalkyl, cycloalkenyl, alkenyl, alkynyl, aralkyl, aryl and heteroaryl;

or R$^{42}$ and R$^{43}$ may be taken together with the nitrogen to which they are attached form a 5- to 7-membered ring which may optionally contain a further heteroatom;

b is 0 to 6;

R$^5$ is selected from the group consisting of H, alkyl, cycloalkyl, alkenyl, alkynyl, aralkyl, aryl, heteroaryl, —(CH$_2$)$_b$C(O)R$^{51}$, —(CH$_2$)$_b$C(O)N(R$^{52}$)(R$^{53}$), and —(CH$_2$)$_b$C(O)OR$^{51}$;

each R$^{51}$ is independently selected from H, alkyl, cycloalkyl, cycloalkenyl, alkenyl, alkynyl, aralkyl, aryl and heteroaryl;

R$^{52}$ and R$^{53}$ are independently selected from H, alkyl, cycloalkyl, cycloalkenyl, alkenyl, alkynyl, aralkyl, aryl and heteroaryl;

or R$^{52}$ and R$^{53}$ may be taken together with the nitrogen to which they are attached form a 5- to 7-membered ring which may optionally contain a further heteroatom; and b is 0 to 6;

or a pharmaceutically acceptable salt or hydrate thereof.

In a further embodiment of the invention, X of a compound according to formula XI is selected to be a O to give a compound of the formula XII:

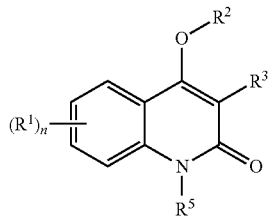

(XII)

wherein:

each R$^1$ is independently selected from alkyl, alkenyl, alkynyl, aralkyl, —O—R$^{11}$, —N(R$^{12}$)(R$^{13}$), —N(R$^{11}$)C(O)R$^{11}$, —N(R$^{11}$)SO$_2$R$^{11}$, —SR$^{11}$, —C(O)R$^{11}$, —C(O)OR$^{11}$, —C(O)N(R$^{12}$)(R$^{13}$), —OC(O)R$^{11}$, —OC(O)N(R$^{12}$)(R$^{13}$), CN, CF$_3$, NO$_2$, SO$_2$, —SOR$^{11}$, —SO$_3$R$^{11}$, —SO$_2$N(R$^{12}$)(R$^{13}$), -alkyl-O—R$^{11}$, cycloalkyl, cycloalkenyl, halo, phosphate, phosphonate, aryl and heteroaryl;

additionally or alternatively two R$^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from R$^1$;

each R$^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each R$^{12}$ and R$^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or R$^{12}$ and R$^{13}$ may be taken together with the nitrogen to which they are attached form a 5- to 7-membered ring which may optionally contain a further heteroatom, n is 0 to 4;

R$^2$ is selected from the group consisting of aralkyl, aryl, heteroaryl, cycloalkyl and cycloalkenyl;

R$^3$ is selected from the group consisting of alkyl, cycloalkyl, alkenyl, alkynyl, aralkyl, aryl, heteroaryl, —(CH$_2$)$_a$C(O)R$^{31}$, —(CH$_2$)$_a$C(O)N(R$^{32}$)(R$^{33}$), (CH$_2$)$_a$C(O)OR$^{31}$, —(CH$_2$)$_a$C(O)N(R$^{32}$)(R$^{33}$), —(CH$_2$)$_a$N(R$^{32}$)(R$^{33}$), —CH═N—R$^{34}$, R$^{31}$ selected from H, alkyl, cycloalkyl, cycloalkenyl, alkenyl, alkynyl, aralkyl, aryl and heteroaryl;

R$^{32}$ and R$^{33}$ are independently selected from H, alkyl, cycloalkyl, cycloalkenyl, alkenyl, alkynyl, aralkyl, aryl and heteroaryl;

or R$^{32}$ and R$^{33}$ may be taken together with the nitrogen to which they are attached form a 5- to 7-membered ring which may optionally contain a further heteroatom;

R$^{34}$ is selected from alkyl, cycloalkyl, cycloalkenyl, alkenyl, alkynyl, aralkyl, aryl and heteroaryl a is 0 to 6;

R$^5$ is selected from the group consisting of H, alkyl, cycloalkyl, alkenyl, alkynyl, aralkyl, aryl, heteroaryl, —(CH$_2$)$_b$C(O)R$^{51}$, —(CH$_2$)$_b$C(O)N(R$^{52}$)(R$^{53}$), and —(CH$_2$)$_b$C(O)OR$^{51}$;

each R$^{51}$ is independently selected from H, alkyl, cycloalkyl, cycloalkenyl, alkenyl, alkynyl, aralkyl, aryl and heteroaryl;

R$^{52}$ and R$^{53}$ are independently selected from H, alkyl, cycloalkyl, cycloalkenyl, alkenyl, alkynyl, aralkyl, aryl and heteroaryl;

or R$^{52}$ and R$^{53}$ may be taken together with the nitrogen to which they are attached form a 5- to 7-membered ring which may optionally contain a further heteroatom; and b is 0 to 6;

or a pharmaceutically acceptable salt or hydrate thereof.

In further preferred embodiment of the invention, R$^2$ and R$^3$ of a compound according to formula XII are selected to be a —CH$_2$—R$^6$ and —CH$_2$—R$^7$, respectively, to give a compound of the formula XIII:

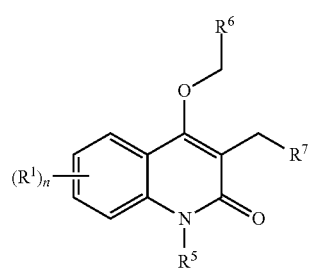

(XIII)

wherein:

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^5$ is selected from the group consisting of H, alkyl, cycloalkyl, alkenyl, alkynyl, aralkyl, aryl, heteroaryl, —(CH$_2$)$_b$C(O)$R^{51}$, —(CH$_2$)$_b$C(O)N($R^{52}$)($R^{53}$), and —(CH$_2$)$_b$C(O)O$R^{51}$, each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

$R^6$ is selected from the group consisting of aryl and heteroaryl;

$R^7$ is selected from the group consisting of aryl, heteroaryl, —C(O)$R^{31}$, —C(O)N($R^{32}$)($R^{33}$), —C(O)O$R^{31}$, —C(O)N($R^{32}$)($R^{33}$), and —N($R^{32}$)($R^{33}$), $R^{31}$ selected from H, alkyl, cycloalkyl, cycloalkenyl, alkenyl, alkynyl, aralkyl, aryl and heteroaryl; and $R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

or a pharmaceutically acceptable salt or hydrate thereof.

In a preferred embodiment for compounds of the formula XIII, $R^6$ is selected to be an aryl or heteroaryl groups.

In another embodiment of the invention, $R^2$ of a compound according to formula XII is selected to be a benzyl group to give a compound of the formula XIV:

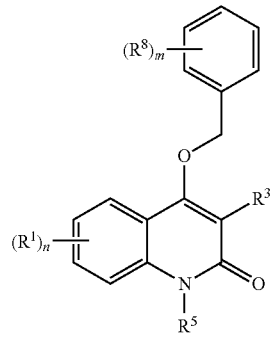

(XIV)

wherein:

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^3$ is selected from the group consisting of alkyl, cycloalkyl, alkenyl, alkynyl, aralkyl, aryl, heteroaryl, —(CH$_2$)$_a$C(O)$R^{31}$, —(CH$_2$)$_a$C(O)N($R^{32}$)($R^{33}$), (CH$_2$)$_a$C(O)O$R^{31}$, —(CH$_2$)$_a$C(O)N($R^{32}$)($R^{33}$), —(CH$_2$)$_a$N($R^{32}$)($R^{33}$), —CH═N—$R^{34}$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

$R^{34}$ is selected from alkyl, cycloalkyl, cycloalkenyl, alkenyl, alkynyl, aralkyl, aryl and heteroaryl a is 0 to 6;

$R^5$ is selected from the group consisting of H, alkyl, cycloalkyl, alkenyl, alkynyl, aralkyl, aryl, heteroaryl, —(CH$_2$)$_b$C(O)$R^{51}$, —(CH$_2$)$_b$C(O)N($R^{52}$)($R^{53}$), and —(CH$_2$)$_b$C(O)O$R^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, $NO_2$, $CO_2R^{81}$, $C(O)R^{81}$, —O—$R^{81}$, —N($R^{82}$)($R^{83}$), —N($R^{81}$)C(O)$R^{81}$, —N($R^{81}$)$SO_2R^{81}$, —$SR^{81}$, —C(O)N($R^{82}$)($R^{83}$), —OC(O)$R^{81}$, —OC(O)N($R^{82'}$)($R^{83}$), $SO_2$, —$SOR^{81}$, —$SO_3R^{81}$, —$SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom; and m is 0 to 5;

or a pharmaceutically acceptable salt or hydrate thereof.

In further preferred embodiment of the invention, $R^6$ and $R^7$ of a compound according to formula XIII are selected to be phenyl groups, to give a compound of the formula XV:

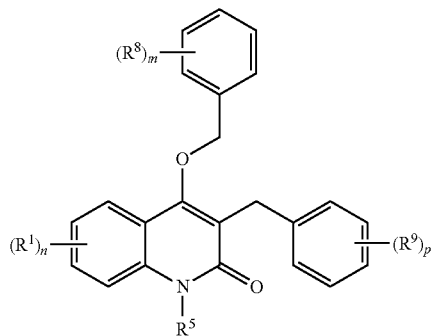

(XV)

wherein:

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)$SO_2R^{11}$, —$SR^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, $CF_3$, $NO_2$, $SO_2$, —$SOR^{11}$, —$SO_3R^{11}$, —$SO_2N(R^{12})(R^{13})$, -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom, n is 0 to 4;

$R^5$ is selected from the group consisting of H, alkyl, cycloalkyl, alkenyl, alkynyl, aralkyl, aryl, heteroaryl, —$(CH_2)_bC(O)R^{51}$, —$(CH_2)_bC(O)N(R^{52})(R^{53})$, and —$(CH_2)_bC(O)OR^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, $NO_2$, $CO_2R^{81}$, $C(O)R^8$, —O—$R^{81}$, —N($R^{82}$)($R^{83}$), —N($R^{81}$)C(O)$R^{81}$, —N($R^{81}$)$SO_2R^{81}$, —$SR^{81}$, —C(O)N($R^{82}$)($R^{83}$), —OC(O)$R^{81}$, —OC(O)N($R^{82'}$)($R^{83}$), $SO_2$, —$SOR^{81}$, —$SO_3R^{81}$, —$SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom;

m is 0 to 5;

each $R^9$ is independently selected from the group consisting of halo, alkyl, CN, $NO_2$, $CO_2R^{91}$, $C(O)R^9$, —O—$R^{91}$, —N($R^{92}$)($R^{93}$), —N($R^{91}$)C(O)$R^{91}$, —N($R^{91}$)$SO_2R^{91}$, —$SR^{91}$, —C(O)N($R^{92}$)($R^{93}$), —OC(O)$R^{91}$, —OC(O)N($R^{92}$)($R^{93}$), $SO_2$, —$SOR^{91}$, —$SO_3R^{91}$, —$SO_2N(R^{92})(R^{93})$, cycloalkyl, cycloalkenyl, aryl and heteroaryl;

each $R^{91}$ is independently selected from H, alkyl, cycloalkyl, cycloalkenyl, alkenyl, alkynyl, aralkyl, aryl and heteroaryl;

each $R^{92}$ and $R^{93}$ are independently selected from H, alkyl, cycloalkyl, cycloalkenyl, alkenyl, alkynyl, aralkyl, aryl and heteroaryl; or $R^{92}$ and $R^{93}$ may be taken together with the nitrogen to which they are attached form a 5- to 7-membered ring which may optionally contain a further heteroatom; and p is 0 to 5;

or a pharmaceutically acceptable salt or hydrate thereof.

Exemplary compounds of the formula XV include the following structures:

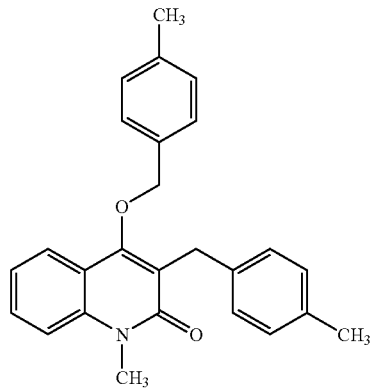

-continued

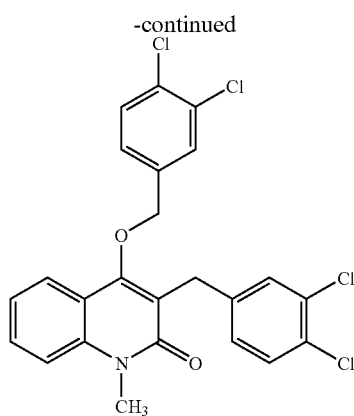

In a another embodiment of the invention, X of a compound according to formula XI is selected to be a N—R⁴ to give a compound of the formula XVI:

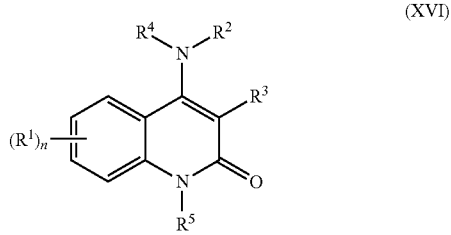

(XVI)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;
each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl; or $R^{12}$ and $R^{13}$ may be taken together with the nitrogen to which they are attached form a 5- to 7-membered ring which may optionally contain a further heteroatom,
n is 0 to 4;
$R^2$ is selected from the group consisting of aralkyl, aryl, heteroaryl, cycloalkyl and cycloalkenyl;
$R^3$ is selected from the group consisting of alkyl, cycloalkyl, alkenyl, alkynyl, aralkyl, aryl, heteroaryl, —(CH$_2$)$_a$C(O)$R^{31}$, —(CH$_2$)$_a$C(O)N($R^{32}$)($R^{33}$), (CH$_2$)$_a$C(O)O$R^{31}$, —(CH$_2$)$_a$C(O)N($R^{32}$)($R^{33}$), —(CH$_2$)$_a$N($R^{32}$)($R^{33}$), —CH═N—$R^{34}$,
$R^{31}$ selected from H, alkyl, cycloalkyl, cycloalkenyl, alkenyl, alkynyl, aralkyl, aryl and heteroaryl;
$R^{32}$ and $R^{33}$ are independently selected from H, alkyl, cycloalkyl, cycloalkenyl, alkenyl, alkynyl, aralkyl, aryl and heteroaryl;
or $R^{32}$ and $R^{33}$ may be taken together with the nitrogen to which they are attached form a 5- to 7-membered ring which may optionally contain a further heteroatom;
$R^{34}$ is selected from alkyl, cycloalkyl, cycloalkenyl, alkenyl, alkynyl, aralkyl, aryl and heteroaryl
a is 0 to 6;
$R^4$ is selected from the group consisting of H, alkyl, cycloalkyl, alkenyl, alkynyl, aralkyl, aryl, heteroaryl, —(CH$_2$)$_b$C(O)$R^{41}$, —(CH$_2$)$_b$C(O)N($R^{42}$)($R^{43}$), —(CH$_2$)$_b$C(O)O$R^{41}$, and —(CH$_2$)$_b$C(O)N($R^{42}$)($R^{43}$),
each $R^{41}$ is independently selected from H, alkyl, cycloalkyl, cycloalkenyl, alkenyl, alkynyl, aralkyl, aryl and heteroaryl;
$R^{42}$ and $R^{43}$ are independently selected from H, alkyl, cycloalkyl, cycloalkenyl, alkenyl, alkynyl, aralkyl, aryl and heteroaryl;
or $R^{42}$ and $R^{43}$ may be taken together with the nitrogen to which they are attached form a 5- to 7-membered ring which may optionally contain a further heteroatom;
b is 0 to 6;
$R^5$ is selected from the group consisting of H, alkyl, cycloalkyl, alkenyl, alkynyl, aralkyl, aryl, heteroaryl, —(CH$_2$)$_b$C(O)$R^{51}$, —(CH$_2$)$_b$C(O)N($R^{52}$)($R^{53}$), and —(CH$_2$)$_b$C(O)O$R^{51}$;
each $R^{51}$ is independently selected from H, alkyl, cycloalkyl, cycloalkenyl, alkenyl, alkynyl, aralkyl, aryl and heteroaryl;
$R^{52}$ and $R^{53}$ are independently selected from H, alkyl, cycloalkyl, cycloalkenyl, alkenyl, alkynyl, aralkyl, aryl and heteroaryl;
or $R^{52}$ and $R^{53}$ may be taken together with the nitrogen to which they are attached form a 5- to 7-membered ring which may optionally contain a further heteroatom; and
b is 0 to 6;
or a pharmaceutically acceptable salt or hydrate thereof.
In further preferred embodiment of the invention, $R^2$ and $R^3$ of a compound according to formula XVI are selected to be a —CH$_2$—$R^6$ and —CH$_2$—$R^7$, respectively, to give a compound of the formula XVII:

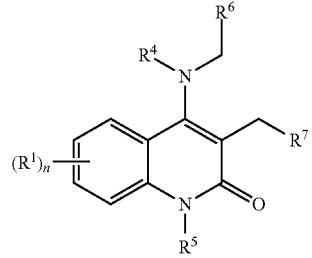

(XVII)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, —S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO$_3R^{11}$, —SO$_2$N($R^{12}$)($R^{13}$), -alkyl-O—$R^{11}$, cycloalkyl, cycloalkenyl, halo, phosphate, phosphonate, aryl and heteroaryl;
additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

$R^5$ is selected from the group consisting of H, alkyl, cycloalkyl, alkenyl, alkynyl, aralkyl, aryl, heteroaryl, —$(CH_2)_bC(O)R^{51}$, —$(CH_2)_bC(O)N(R^{52})(R^{53})$, and —$(CH_2)_bC(O)OR^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

$R^6$ is selected from the group consisting of aryl and heteroaryl;

$R^7$ is selected from the group consisting of aryl, heteroaryl, —$C(O)R^{31}$, —$C(O)N(R^{32})(R^{33})$, —$C(O)OR^{31}$, —$C(O)N(R^{32})(R^{33})$, and —$N(R^{32})(R^{33})$, $R^{31}$ selected from H, alkyl, cycloalkyl, cycloalkenyl, alkenyl, alkynyl, aralkyl, aryl and heteroaryl; and $R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

or a pharmaceutically acceptable salt or hydrate thereof.

In a preferred embodiment for compounds of the formula XVII, $R^6$ is selected to be an aryl or heteroaryl groups.

In another embodiment of the invention, $R^2$ of a compound according to formula XVI is selected to be a benzyl group to give a compound of the formula XVIII:

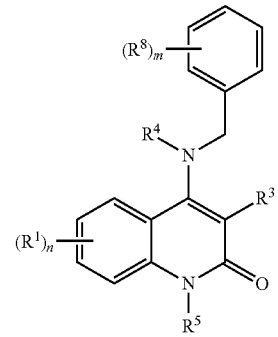

(XVIII)

wherein:

each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, —$SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $S_2$, —$SOR^{11}$, —$SO_3R^{11}$, —$SO_2N(R^{12})(R^{13})$, -alkyl-O—$R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered membered ring which may optionally contain a further heteroatom, n is 0 to 4;

$R^3$ is selected from the group consisting of alkyl, cycloalkyl, alkenyl, alkynyl, aralkyl, aryl, heteroaryl, —$(CH_2)_aC(O)R^{31}$, —$(CH_2)_aC(O)N(R^{32})(R^{33})$, $(CH_2)_aC(O)OR^{31}$, —$(CH_2)_aC(O)N(R^{32})(R^{33})$, —$(CH_2)_aN(R^{32})(R^{33})$, —CH=N—$R^{34}$, $R^{31}$ selected from H, alkyl, cycloalkyl, cycloalkenyl, alkenyl, alkynyl, aralkyl, aryl and heteroaryl;

$R^{32}$ and $R^{33}$ are independently selected from H, alkyl, cycloalkyl, cycloalkenyl, alkenyl, alkynyl, aralkyl, aryl and heteroaryl;

or $R^{32}$ and $R^{33}$ may be taken together with the nitrogen to which they are attached form a 5- to 7-membered ring which may optionally contain a further heteroatom;

$R^{34}$ is selected from alkyl, cycloalkyl, cycloalkenyl, alkenyl, alkynyl, aralkyl, aryl and heteroaryl a is 0 to 6;

$R^4$ is selected from the group consisting of H, alkyl, cycloalkyl, alkenyl, alkynyl, aralkyl, aryl, heteroaryl, —$(CH_2)_bC(O)R^{41}$, —$(CH_2)_bC(O)N(R^{42})(R^{43})$, —$(CH_2)_bC(O)OR^{41}$, and —$(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

$R^5$ is selected from the group consisting of H, alkyl, cycloalkyl, alkenyl, alkynyl, aralkyl, aryl, heteroaryl, $-(CH_2)_bC(O)R^{51}$, $-(CH_2)_bC(O)N(R^{52})(R^{53})$, and $-(CH_2)_bC(O)OR^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, $NO_2$, $CO_2R^{81}$, $C(O)R^{81}$, $-O-R^{81}$, $-N(R^{82})(R^{83})$, $-N(R^{81})C(O)R^{81}$, $-N(R^{81})SO_2R^{81}$, $-SR^{81}$, $-C(O)N(R^{82})(R^{83})$, $-OC(O)R^{81}$, $-OC(O)N(R^{82'})(R^{83})$, $SO_2$, $-SOR_{81}$, $-SO_3R^{81}$, $-SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom; and m is 0 to 5;

or a pharmaceutically acceptable salt or hydrate thereof.

In further preferred embodiment of the invention, $R^6$ and $R^7$ of a compound according to formula XVII are selected to be phenyl groups, to give a compound of the formula XIX:

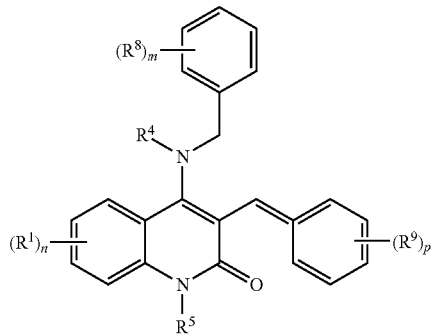

(XIX)

wherein:

each $R^1$ is independently selected from alkyl, alkenyl, alkynyl, aralkyl, $-O-R^{11}$, $-N(R^{12})(R^{13})$, $-N(R^{11})C(O)R^{11}$, $-N(R^{11})SO_2R^{11}$, $-SR^{11}$, $-C(O)R^{11}$, $-C(O)OR^{11}$, $-C(O)N(R^{12})(R^{13})$, $-OC(O)R^{11}$, $-OC(O)N(R^{12})(R^{13})$, CN, $CF_3$, $NO_2$, $SO_2$, $-SOR^{11}$, $-SO_3R^{11}$, $-SO_2N(R^{12})(R^{13})$, -alkyl-$O-R^{11}$, cycloalkyl, cycloalkenyl, halo, phosphate, phosphonate, aryl and heteroaryl;

additionally or alternatively two $R^1$ substituents on adjacent ring atoms my be combined to form a fused 5 or 6-membered ring, wherein the fused 5- or 6-membered ring may contain from 0 to 3 ring heteroatoms and may be further substituted with on or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, aryl and heteroaryl;

each $R^{12}$ and $R^{13}$ are independently selected from H, alkyl, cycloalkyl, cycloalkenyl, alkyl-O-alkyl, alkyl-O-aryl, alkenyl, alkynyl, aralkyl, aryl and heteroaryl;

or $R^{12}$ and $R^{13}$ may be taken together with the nitrogen to which they are attached form a 5- to 7-membered ring which may optionally contain a further heteroatom, n is 0 to 4;

$R^4$ is selected from the group consisting of H, alkyl, cycloalkyl, alkenyl, alkynyl, aralkyl, aryl, heteroaryl, $-(CH_2)_bC(O)R^{41}$, $-(CH_2)_bC(O)N(R^{42})(R^{43})$, $-(CH_2)_bC(O)OR^{41}$, and $-(CH_2)_bC(O)N(R^{42})(R^{43})$, each $R^{41}$ is independently selected from H, alkyl, cycloalkyl, cycloalkenyl, alkenyl, alkynyl, aralkyl, aryl and heteroaryl;

$R^{42}$ and $R^{43}$ are independently selected from H, alkyl, cycloalkyl, cycloalkenyl, alkenyl, alkynyl, aralkyl, aryl and heteroaryl;

or $R^{42}$ and $R^{43}$ may be taken together with the nitrogen to which they are attached form a 5- to 7-membered ring which may optionally contain a further heteroatom;

b is 0 to 6;

$R^5$ is selected from the group consisting of H, alkyl, cycloalkyl, alkenyl, alkynyl, aralkyl, aryl, heteroaryl, $-(CH_2)_bC(O)R^{51}$, $-(CH_2)_bC(O)N(R^{52})(R^{53})$, and $-(CH_2)_bC(O)OR^{51}$;

each $R^{51}$ is independently selected from H, alkyl, cycloalkyl, cycloalkenyl, alkenyl, alkynyl, aralkyl, aryl and heteroaryl;

$R^{52}$ and $R^{53}$ are independently selected from H, alkyl, cycloalkyl, cycloalkenyl, alkenyl, alkynyl, aralkyl, aryl and heteroaryl;

or $R^{52}$ and $R^{53}$ may be taken together with the nitrogen to which they are attached form a 5- to 7-membered ring which may optionally contain a further heteroatom;

b is 0 to 6;

each $R^8$ is independently selected from the group consisting of halo, alkyl, CN, $NO_2$, $CO_2R^{81}$, $C(O)R^{81}$, $-O-R^{81}$, $-N(R^{82})(R^{83})$, $-N(R^{81})C(O)R^{81}$, $-N(R^{81})SO_2R^{81}$, $-SR^{81}$, $-C(O)N(R^{82})(R^{83})$, $-OC(O)R^{81}$, $-OC(O)N(R^{82'})(R^{83})$, $SO_2$, $-SOR^{81}$, $-SO_3R^{81}$, $-SO_2N(R^{82})(R^{83})$, cycloalkyl, cycloalkenyl, aryl and heteroaryl;

each $R^{81}$ is independently selected from H, alkyl, cycloalkyl, cycloalkenyl, alkenyl, alkynyl, aralkyl, aryl and heteroaryl;

each $R^{82}$ and $R^{83}$ are independently selected from H, alkyl, cycloalkyl, cycloalkenyl, alkenyl, alkynyl, aralkyl, aryl and heteroaryl; or $R^{82}$ and $R^{83}$ may be taken together with the nitrogen to which they are attached form a 5- to 7-membered ring which may optionally contain a further heteroatom;

m is 0 to 5;

each $R^9$ is independently selected from the group consisting of halo, alkyl, CN, $NO_2$, $CO_2R^{91}$, $C(O)R^{91}$, $-O-R^{91}$, $-N(R^{92})(R^{93})$, $-N(R^{91})C(O)R^{91}$, $-N(R^{91})SO_2R^{91}$, $-SR^{91}$, $-C(O)N(R^{92})(R^{93})$, $-OC(O)R^{91}$, $-OC(O)N(R^{92})(R^{93})$, $SO_2$, $-SOR^{91}$, $-SO_3R^{91}$, $-SO_2N(R^{92})(R^{93})$, cycloalkyl, cycloalkenyl, aryl and heteroaryl;

each $R^{91}$ is independently selected from H, alkyl, cycloalkyl, cycloalkenyl, alkenyl, alkynyl, aralkyl, aryl and heteroaryl;

each $R^{92}$ and $R^{93}$ are independently selected from H, alkyl, cycloalkyl, cycloalkenyl, alkenyl, alkynyl, aralkyl, aryl and heteroaryl; or $R^{92}$ and $R^{93}$ may be taken together with the nitrogen to which they are attached, form a 5- to 7-membered ring which may optionally contain a further heteroatom; and p is 0 to 5;

or a pharmaceutically acceptable salt or hydrate thereof.

The substances according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19.)

When one or more chiral centers are present in the compounds of the present invention, the individual isomers and mixtures thereof (e.g., racemates, etc.) are intended to be encompassed by the formulae depicted herein. In certain embodiments, compounds of the invention may exist in several tautomeric forms. Accordingly, the chemical structures depicted herein encompass all possible tautomeric forms of the illustrated compounds. Compounds of the invention may exist in various hydrated forms.

It is understood that when n is a value greater than 1, each $R^1$ group may be selected independently. Thus, when more than one $R^1$ group is present, the $R^1$ groups may be selected from any of the stated groups so as to be the same or different. This also holds true for any other group or substituent which may be selected independently from among various groups or values.

In another aspect of the invention, a synthetic process for the preparation of compounds of the invention is provided. The inventive process uses mild reaction conditions, which provides a high substituent tolerance. The product is obtained in high yield and high purity. A process of the present invention is illustrated by Scheme I:

Scheme 1

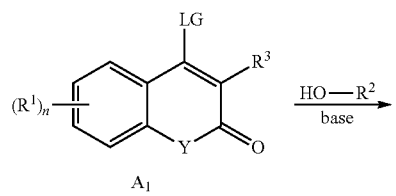

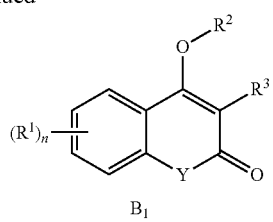

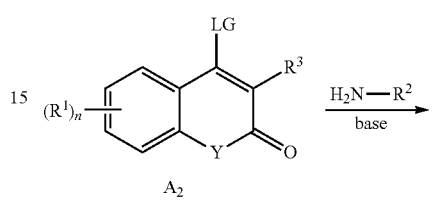

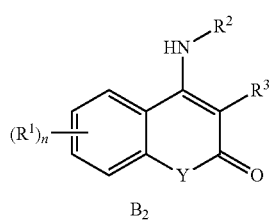

$A_1$ and $A_2$ may be treated with an alcohol (HO—$R^2$) or amine ($H_2N$—$R^2$) in the presence of an appropriate base. LG represents a leaving group, such as halo, aryl sulfones (tosyl, etc.), triflate or other appropriate leaving group as would be recognized by the ordinarily skilled practitioner. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

In other embodiments, compounds of the invention may be prepared according the reactions provided in Scheme 2:

Scheme 2

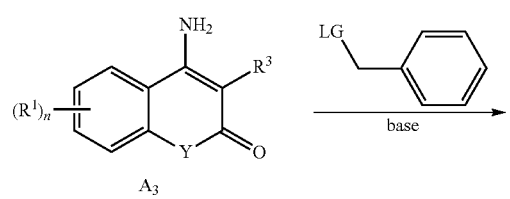

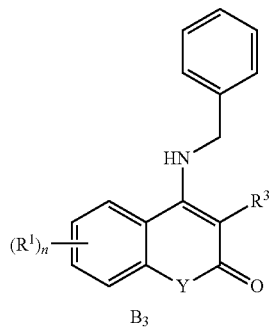

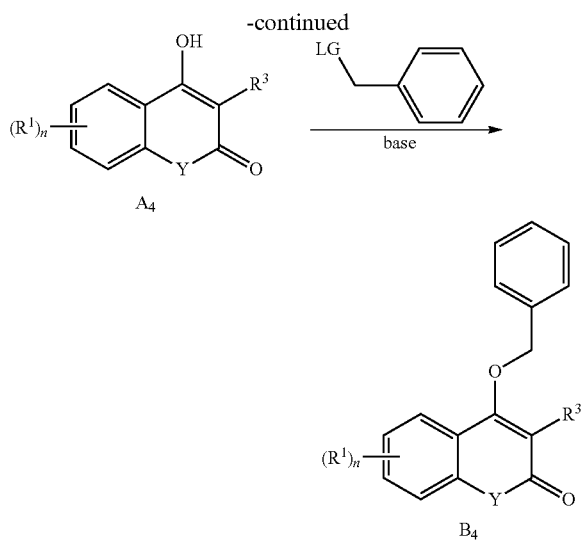

A₃ and A₄ may be treated with an activated benzyl group in the presence of an appropriate base. LG represents a leaving group, such as halo, aryl sulfones (tosyl, etc.), triflate or other appropriate leaving group as would be recognized by the ordinarily skilled practitioner. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

In other embodiments, compounds of the invention may be prepared in the manner described in Scheme 3:

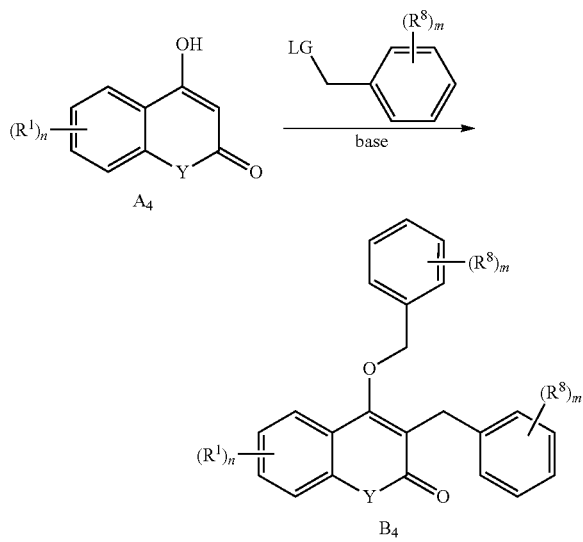

A₄ may be treated with an activated benzyl group in the presence of an appropriate base. LG represents a leaving group, such as halo, aryl sulfones (tosyl, etc.), triflate or other appropriate leaving group as would be recognized by the ordinarily skilled practitioner. The base may be selected from amine bases, hydroxide salts (non-limiting examples include sodium hydroxide and tetraalkylamonium hydroxides), carbonate salts, hydrides, alkoxide salts (non-limiting examples include sodium methoxide and potassium t-butoxide) and the like.

It may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

The compounds and processes disclosed herein are useful in the production of a library of 3,4-disubstituted coumarin and quinolone derivatives for biological screening. Derivatives of coumarin and quinolone posses a range of biological activities. Coumarin-based and quinolone-based compounds have shown efficacy, for example, as antivirals. Particularly, the compounds of the present invention may be used to prevent or treat infection with HCV.

The identification of inhibitors of HCV replication and/or proliferation has been facilitated by the development of a cell based system to study HCV replication and assay for HCV inhibitors. Inhibition of HCV replication may be performed using the HCV Replicon Assay developed in the laboratories of Bartenschlager (Lohman et al, *Science* 285, 110-113, 1999) and Rice (Blight et al, *Science* 290, 1972-1974, 2000). The assay is performed using the Huh-Luc-Neo cell line (Lohman et al, *Science* 285, 110-113, 1999). Huh-Luc-Neo cells are a human hepatoma cell line (Huh-7) stably expressing a bi-cistronic subgenomic replicon containing the HCV IRES in which the structural proteins of HCV had been deleted and replaced by a construct containing sequences coding for the firefly luciferase reporter gene, the neomycin selectable marker and the EMCV IRES to direct expression of a truncated HCV genome expressing the structural proteins NS3, NS4A, NS4B, NS5A, and NS5B. HCV targets through which inhibitors could act to inhibit replication include the NS3 protease, the helicase/ATPase, NS5A, the NS5B- RNA dependent RNA polymerase, and the HCV IRES.

Expression of HCV IRES driven luciferase reporter activity and HCV RNA is measured to obtain indirect and direct measures of replication of HCV RNA respectively. Inhibitors of HCV replication and/or proliferation are determined by initially identifying molecules that inhibit expression of the HCV IRES driven luciferase reporter in this HCV Replicon Luciferase Assay. Cell viability assays and control cell based luciferase assays are then run on hits identified in the HCV Replicon Luciferase Assay to eliminate cytoxic compounds and non-specific compounds which act by inhibiting the luciferase enzyme. Validated inhibitors of HCV replication and/or proliferation are identified by evaluating HCV Replicon Luciferase hits that are specific and non-cytoxic and demonstrating that these compounds inhibit expression of HCV RNA using a quantitative PCR based approach (Taqman) using primers and probes specific for HCV RNA (HCV Replicon RNA Assay).

The HCV Replicon Assay may be used to predict compound efficacy in treatment and/or prevention of HCV infection as well as inhibition of HCV replication and/or proliferation. The HCV Replicon encompasses a multiplicity of viral and host targets through which an inhibitor could work to inhibit HCV Replication. Viral targets expressed in the HCV Replicon include the HCV IRES (for translation), NS3 Protease, the HCV Helicase/ATPase, NS5A phosphorylation, and the NS5B polymerase. Without being limited to theory, it is believed that the compounds of the present invention inhibit HCV replication. The compounds of the invention may inhibit replication as by acting on the IRES, NS3 protease, NS5B polymerase, Helicase/ATPase, or NS5A phosphorylation.

Thus, in another embodiment, the present invention provides pharmaceutical compositions comprising an anti-HCV effective amount of a compound of formula I, or a pharmaceutically acceptable salt or hydrate thereof, in combination with a pharmaceutically acceptable carrier or auxiliary agent. As used herein, the terms "pharmaceutically acceptable salts" and "hydrates" refer to those salts and hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity and flowability of the resulting bulk drug.

The invention also provides a method of treating HCV infection in a mammal, preferable a human, by administering to the mammal an effective amount of a compound of the present invention, a pharmaceutically acceptable salt or hydrate thereof, or a composition as described above. The compounds of the invention may be administered alone or may be administered in combination with other approved therapeutics, such as: an interferon (pegylated or not), preferably α-interferon, ribavirin, or interferon and ribavirin, or one or more other anti-HCV agent, such as an HCV protease inhibitor, HCV polymerase inhibitor, HCV IRES inhibitor, HCV Helicase and/or ATPase inhibitor, NS5A phosphorylation inhibitor, HCV NS2 inhibitor, or other HCV life cycle inhibitor. Combination therapies with may include a compound of the invention with multiple different inhibitors of HCV life cycle (immunomodulatory agents, Toll Like Receptor modulators, antisense therapeutics etc.). The agents that comprise a combination therapy may be administered together or separately, e.g., prior to, concurrently with or following the administration of the compound of the invention or pharmaceutically acceptable salt thereof. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

The compounds of the present invention may be employed in solid or liquid form including, for example, amorphous powder or crystalline form, in solution or in suspension. They may be administered in numerous different ways, such as orally, parenterally, topically, transdermally or by inhalation. Oral administration or administration by injection is preferred. The choice of carrier and the content of active compound in the carrier are generally determined in accordance with the solubility and chemical properties of the desired product, the particular mode of administration and well established pharmaceutical practice. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrastemal, intrathecal, and intralesional injection or infusion techniques.

Examples of liquid carriers include syrups, peanut oil, olive oil, water, saline and the like. For parenteral administration, emulsions, suspensions or solutions of the compounds according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, may be used. Injectable forms must be fluid to the extent they can be easily syringed, and proper fluidity can be maintained, for example, by the use of a coating such as lecithin, by the maintenance of the required particle size in the case of dispersion and by the use of surfactants. Prolonged absorption of the injectable compositions can be brought about by use of agents delaying absorption, for example, aluminum monostearate and gelatin. The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. Compounds of the invention may be enclosed in hard or soft shell gelatin capsules, or compressed into tablets. Examples of oral liquid dosage forms include solutions, suspensions, syrups, emulsions, soft gelatin capsules and the like. Carriers for oral use (solid or liquid) may include time delay materials known in the art, such as glyceryl monostearate or glyceryl distearate alone or with a wax. To prepare a capsule, it may be advantageous to use lactose and a liquid carrier, such as high molecular weight polyethylene glycols.

Compositions and dosage forms prepared in accordance with the present invention optionally may contain lactose, sodium citrate, calcium carbonate, dicalcium phosphate and disintegrating agents such as starch, alginic acids and certain complex silica gels combined with lubricants such as magnesium stearate, sodium lauryl sulfate and talc may be used for preparing tablets, capsules and the like. Various other materials may be present as coatings or to otherwise modify the physical form of the dosage unit. For instance, tablets, and capsules may be coated with shellac, sugar or both. When aqueous suspensions are used they may contain emulsifying agents or agents which facilitate suspension. Diluents such as sucrose, ethanol, polyols such as polyethylene glycol, propylene glycol and glycerol, and mixtures thereof also may be used. In addition, the active compound may be incorporated into sustained-release preparations and formulations. If desired, certain sweetening and/or flavoring and/or coloring agents may be added. Other suitable vehicles or carriers for the above noted formulations and compositions can be found in standard pharmaceutical texts, e.g. in "Remington's Pharmaceutical Sciences", The Science and Practice of Pharmacy, 19.sup.th Ed. Mack Publishing Company, Easton, Pa., (1995).

When these compounds or their pharmaceutically acceptable salts are formulated together with a pharmaceutically acceptable carrier, the resulting composition may be administered in vivo to mammals, such as man, to treat or prevent HCV virus infection. Such treatment may also be achieved using a compound of this invention in combination with other anti-viral agents which include, but are not limited to a-interferon and ribavirin. The additional agents may be combined with compounds of this invention to create a single dosage form. Alternatively these additional agents may be separately administered to a mammal as part of a multiple dosage form.

EXAMPLES

General Methods

Reaction solvents were commercially purchased from Acros and Aldrich without further purification and reagents were used as received. Reactions for the synthesis of the starting material were monitored by thin-layer chromatography (TLC) on 0.25 mm precoated Merck Silica Gel 60 $F_{254}$, visualizing with ultraviolet light or phosphomolybdic acid stain. Flash column chromatography was performed on Merck Silica Gel 60 (230-400 mesh) using reagent grade hexanes, dichloromethane, methanol and ethyl acetate.

Reaction reagents were commercially purchased from Alrich and used as received. $^1$H and $^{13}$C NMR spectra were recorded on a Varian 500 MHz spectrometer and are referenced to residual solvent peaks or to an internal reference of tetramethylsilane in $CDCl_3$. LC-MS were obtained on a Micromass ZQ mass spectrameter in ES+ mode with a Water 2790 HPLC system. HPLC condition: C18 column (3.5 μm, 2.1×50 mm, W93491F 26) using a flow rate of 0.4 mL/min in a gradient of 15~100% $CH_3CN$ in H2O in 9 min with 1 min wash.

Example 1

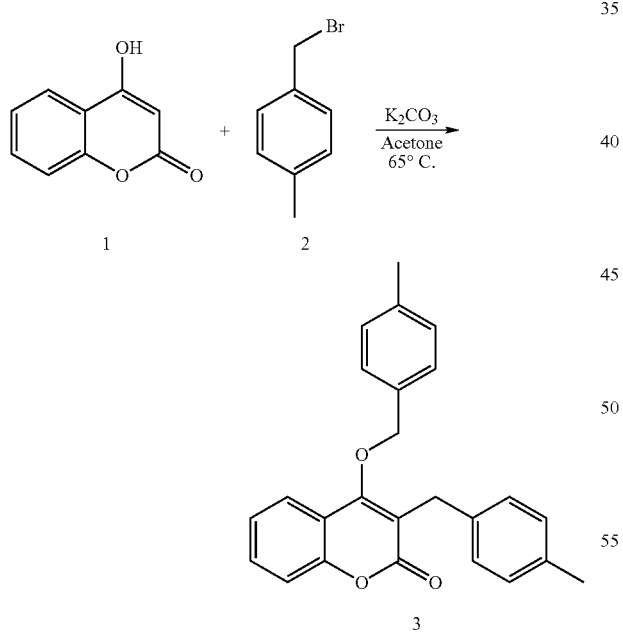

To the mixture of 1 (60 mg, 0.37 mmol) and $K_2CO_3$ (100 mg, 0.73 mmol) in acetone (3 mL), 2 (103 mg, 0.56 mmol) was added slowly. Then the reaction was stirred at 65° C. overnight. After cooled down, and filtered, the solvent was removed, the given residue was purified using PTLC (eluent: EtOAc/Petroleum ether=1:3) to give 3 (13.9 mg, 10%) as solid.

VQ_31711

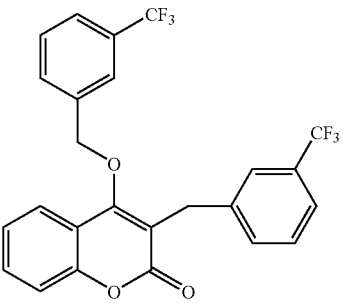

LC-MS (6.77 min, ES$^+$): calcd: 478.10; Found: 479.48. $^1$H NMR ($CDCl_3$): 7.72~7.63 (m, 2H), 7.62~7.52 (m, 3H), 7.52~7.43 (m, 2H), 7.43~7.34 (m, 3H), 7.314 (t, J=7.5 Hz, 1H), 5.13 (s, 2H), 3.977 (s, 2H).

VQ_31712

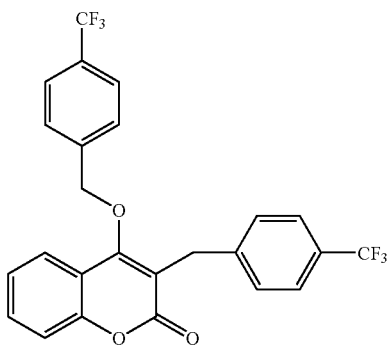

LC-MS (6.81 min, ES$^+$): calcd: 478.10; Found: 479.41. $^1$H NMR ($CDCl_3$): 7.656 (d, J=8 Hz, 1H), 7.627 (AABB, J=80.5, 8.5 Hz, 4H), 7.57 (t, J=7.5 Hz, 1H), 7.455 (AABB, J=52, 8 Hz, 4H), 7.403 (d, J=8 Hz, 1H), 7.309 (t, J=7.5 Hz, 1H), 5.138 (s, 2H), 3.978 (s, 2H).

VQ_31715

LC-MS (6.65 min, ES$^+$): calcd: 370.16; Found: 371.45. $^1$H NMR ($CDCl_3$): 7.72 (d, J=8.5 Hz, 1H), 7.523 (t, J=8.5 Hz, 1H), 7.376 (d, J=8 Hz, 1H), 7.297 (t, J=8 Hz, 1H), 7.31 (AABB, J=45.5, 9.5 Hz, 4H), 7.175 (AABB, J=81.5, 8 Hz, 4H), 5.072 (s, 2H), 3.913 (s, 2H), 2.421 (s, 3H), 2.314 (s, 3H).

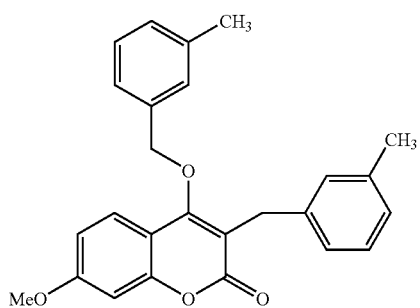

VQ_31729

LC-MS (6.68 min, ES⁺): calcd: 400.17; Found: 401.47. ¹H NMR (CDCl₃): 7.589 (d, J=8.5 Hz, 1H), 7.325 (d, J=7.5 Hz, 1H), 7.31 (d, J=8.5 Hz, 1H), 7.224 (s, 1H), 7.216 (d, J=8.0 Hz, 1H), 7.171~7.115 (m, 3H), 6.999 (d, J=7.5 Hz, 1H), 6.857~6.835 (m, 2H), 5.006 (s, 2H), 3.890 (s, 2H), 3.874 (s, 3H), 2.4 (s, 3H), 2.298 (s, 3H).

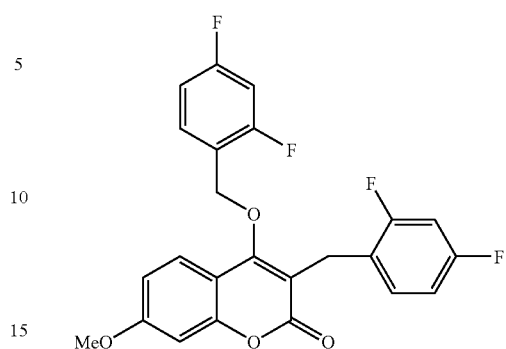

VQ_31744

LC-MS (6.33 min, ES⁺): calcd: 444.10; Found: 445.46. ¹H NMR (CDCl₃): 7.576 (d, J=9 Hz, 1H), 7.428 (q, J=15.5, 8 Hz, 1H), 7.223 (q, J=15, 8 Hz, 1H), 6.937 (t, J=7.5 Hz, 1H), 6.9~6.82 (m, 3H), 6.763 (tt, J=8.5, 2H), 5.078 (s, 2H), 3.825 (s, 5H).

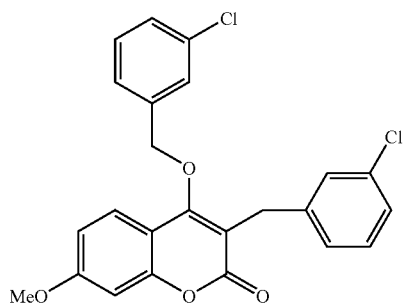

VQ_31734

LC-MS (6.71 min, ES⁺): calcd: 440.06; Found: 441.38. ¹H NMR (CDCl₃): 7.542 (d, J=9.5 Hz, 1H), 7.412 (s, 1H), 7.371 (s, 1H), 7.4~7.35 (m, 1H), 7.3~7.24 (m, 2H), 7.2~7.15 (m, 3H), 6.9~6.85 (m, 2H), 5.002 (s, 2H), 3.879 (s, 3H), 3.861 (s, 2H).

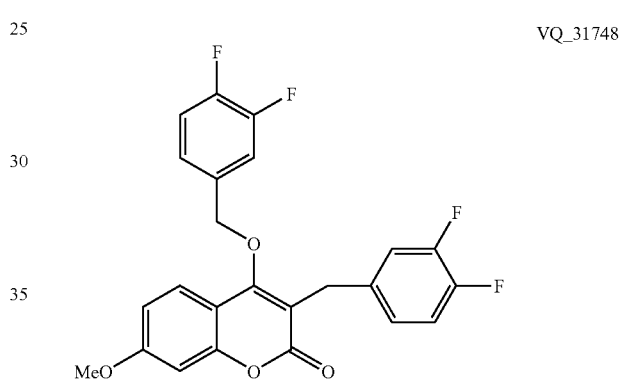

VQ_31748

LC-MS (6.51 min, ES⁺): calcd: 444.10; Found: 445.41. ¹H NMR (CDCl₃): 7.516 (d, J=9.5 Hz, 1H), 7.3~7.16 (m, 2H), 7.15~6.94 (m, 4H), 6.9~6.83 (m, 2H), 5.009 (s, 2H), 3.884 (s, 3H), 3.808 (s, 2H).

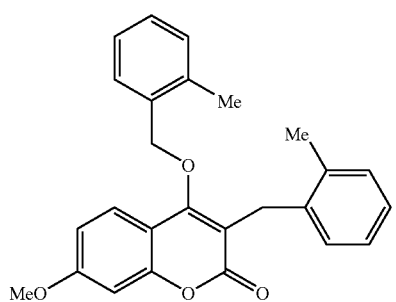

VQ_31738

LC-MS (6.64 min, ES⁺): calcd: 400.17; Found: 401.47. ¹H NMR (CDCl₃): 7.595 (d, J=9.0 Hz, 1H), 7.4~7.25 (m, 3H), 7.25~7.15 (m, 2H), 7.15~7.05 (m, 3H), 6.95~6.85 (m, 2H), 5.01 (s, 2H), 3.886 (s, 3H), 3.872 (s, 2H), 2.33 (s, 3H), 2.207 (s, 3H).

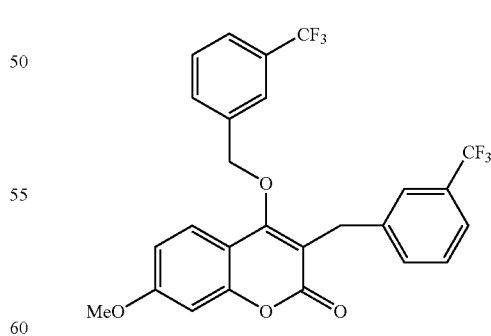

VQ_31754

LC-MS (6.78 min, ES⁺): calcd: 508.11; Found: 509.46. ¹H NMR (CDCl₃): 7.7~7.63 (m, 2H), 7.6~7.5 (m, 4H), 7.5~7.42 (2H), 7.4~7.33 (m, 1H), 6.85~6.82 (m, 2H), 5.097 (s, 2H), 3.939 (s, 2H), 3.885 (s, 3H).

VQ_31758

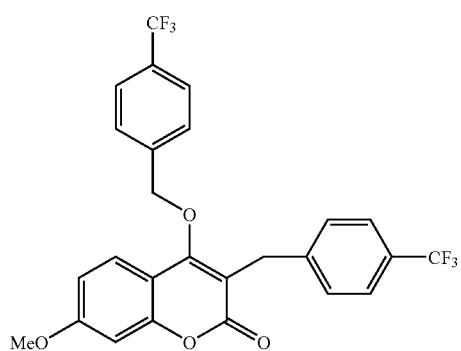

LC-MS (6.84 min, ES⁺): calcd: 508.11; Found: 509.45. ¹H NMR (CDCl₃): 7.614 (AABB, J=85.5, 8.5 Hz, 4H), 7.53 (d, J=8 Hz, 1H), 7.446 (AABB, J=55, 8 Hz, 4H), 6.875 (s, 1H), 6.866 (d, J=8 Hz, 1H), 5.106 (s, 2H), 3.94 (s, 2H), 3.884 (s, 3H).

VQ_31763

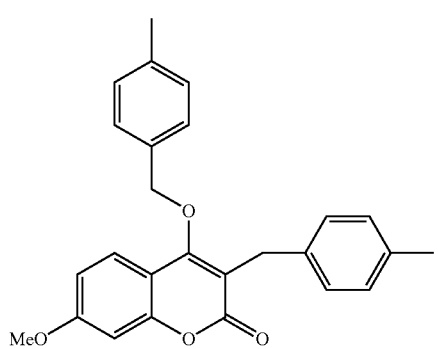

LC-MS (6.68 min, ES⁺): calcd: 400.17; Found: 401.47. ¹H NMR (CDCl₃): 7.576 (d, J=8 Hz, 1H), 7.226 (AABB, J=8, 4 Hz, 4H), 7.19 (AABB, J=121, 8 Hz, 4H), 6.845 (s, 1H), 6.837 (d, J=8 Hz, 1H), 5.028 (s, 2H), 3.869 (s, 3H), 3.859 (s, 2H), 2.40 (s, 3H), 2.294 (s, 3H).

VQ_32806

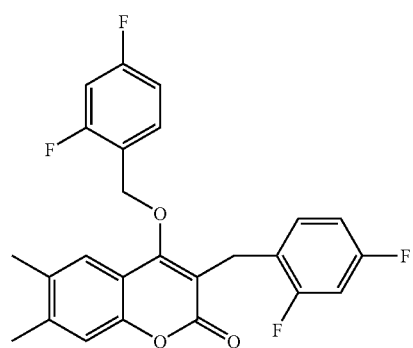

LC-MS (6.64 min, ES⁺): calcd: 442.12; Found: 443.40. ¹H NMR (CDCl₃): 7.438 (q, J=14.5, 8 Hz, 1H), 7.41 (s, 1H), 7.21 (q, J=15.5, 8.5 Hz, 1H), 7.16 (s, 1H), 6.942 (t, J=8 Hz, 1H), 6.881 (t, J=8 Hz, 1H), 6.81~6.7 (m, 2H), 5.081 (s, 2H), 3.882 (s, 2H), 2.36 (s, 3H), 2.306 (s, 3H).

Example 2

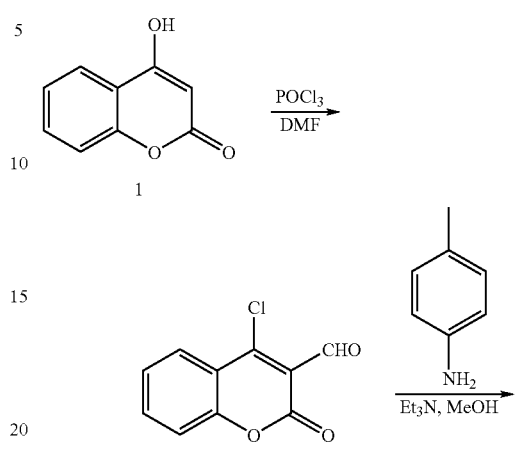

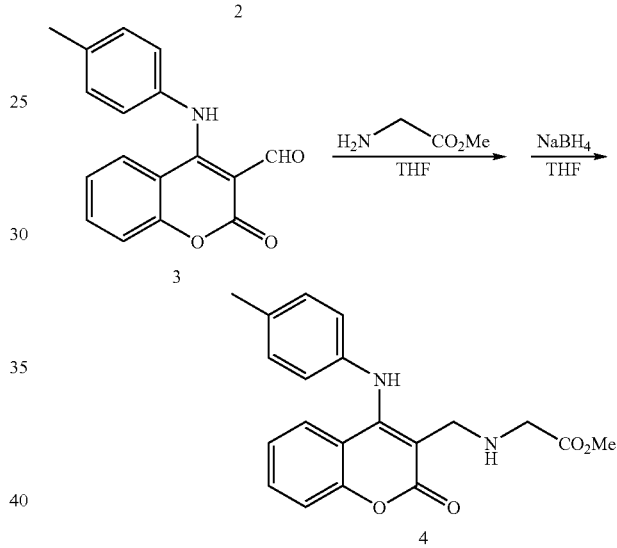

POCl₃ was added slowly to the solution of 1 in DMF at −5~−10° C. (ice bath). Then the mixture stirred for 1 hr at r.t. and for another 2 hrs at 60° C. After cooling down, the mixture was poured to the crushed ice in the flask and stored at 0° C. overnight. Then filtered, and washed down with 5% Na₂CO₃ solution and water followed by drying in vacuum to give 2.

4-Methyl aniline was dissolved in MeOH and added slowly to the mixture of 2 and Et₃N in MeOH and in a couple minutes the precipitation of 3 formed. After filtration, washing down with MeOH, and drying in vacuum amine was added to the solution 3 in THF and the mixture stirred overnight followed adding NaBH₄ to acquired 4. And VQ36344 is the result of the direct reduction of 3.

VQ_36341

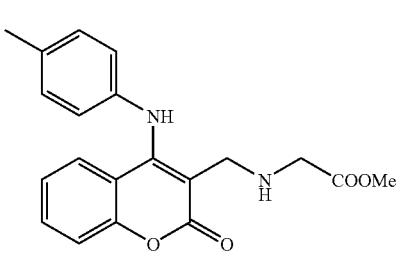

¹H NMR (CDCl₃): 7.581 (br, 1H), 7.44 (t, J=7.5 Hz, 1H), 7.351 (d, J=7.5 Hz, 1), 7.301 (d, J=7.5 Hz, 1H), 7.023 (t, J=7.5 Hz, 1H), 7.017 (AABB, J=93, 7.5 Hz, 4H), 4.733 (s, 2H), 4.2 (br, 1H), 3.818 (s, 3H), 3.614 (d, J=7.5 Hz, 1H), 3.60 (d, J=6.5 Hz, 1H), 2.339 (s, 3H).

VQ_36343

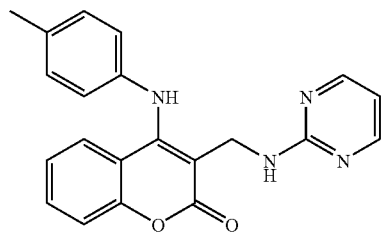

¹H NMR (CDCl₃): 8.471 (s, 1H), 8.394 (d, J=4.5 Hz, 1H), 7.579 (br, 1H), 7.437 (t, J=7.5 Hz, 1H), 7.35 (d, J=8.5 Hz, 1H), 7.30 (d, J=8.5 Hz, 1H), 7.022 (t, J=7.0 Hz, 1), 7.014 (AABB, J=93.5, 8.0 Hz, 4H), 6.725 (t, J=6.0 Hz, 1H), 4.737 (s, 2H), 2.338 (s, 3H).

VQ_36344

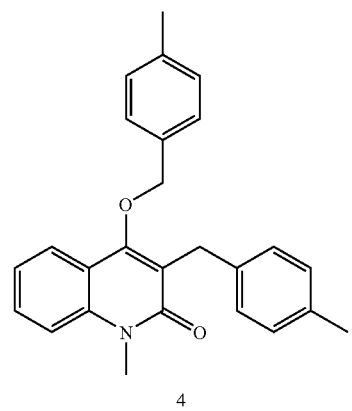

¹H NMR (CDCl₃): 7.456 (t, J=8.0 Hz, 1H), 7.411 (d, J=8.0 Hz, 1H), 7.355 (d, J=8.0 Hz, 1H), 7.124 (t, J=8.0 Hz, 1H), 6.975 (AABB, J=132.5, 7.5 Hz, 4H), 6.064 (br, 1H), 2.333 (s, 3H), 2.031 (s, 3H).

Example 3

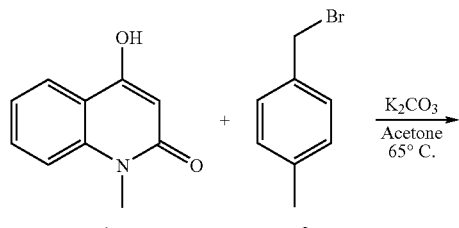

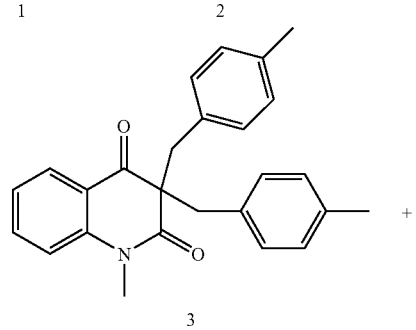

To the mixture of 1 (50 mg, 0.285 mmol) and K₂CO₃ (197 mg, 1.43 mmol) in acetone (3 mL), 2 (158 mg, 0.854 mmol) was added slowly. Then the reaction was stirred at 65° C. overnight. After cooled down, and filtered, the solvent was removed, the given residue was purified using PTLC (eluent: EtOAc/Petroleum ether=1:3) to give 3 (81.3 mg, 74.3%) and 4 (23.2 mg, 21.2%) as solids.

VQ_32833

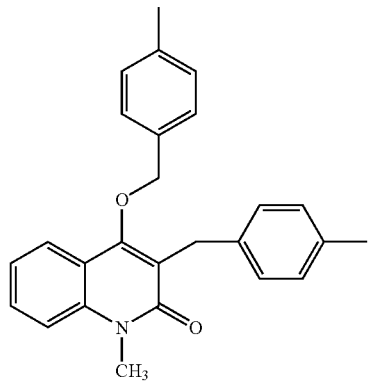

LC-MS (6.42 min, ES⁺): calcd: 383.48; Found: 384.39. ¹H NMR (CDCl₃): 7.85 (dd, J=8.0, 2.0 Hz, 1H), 7.326 (dt, J=9.0, 2.0 Hz, 1H), 6.961 (t, J=7.5 Hz, 1H), 6.88 (AABB, J=46, 8.5 Hz, 8H), 6.66 (d, J=8.5 Hz, 1H), 3.42 (s, 2H), 3.188 (s, 2H), 2.146 (s, 6H).

Example 4

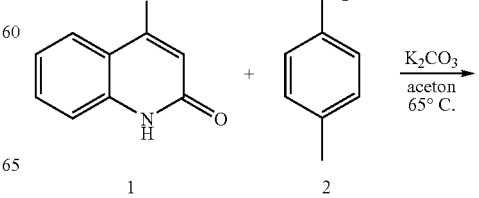

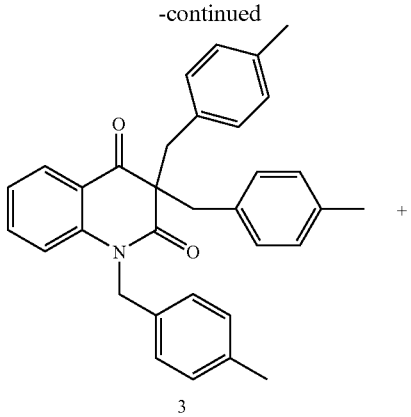

3

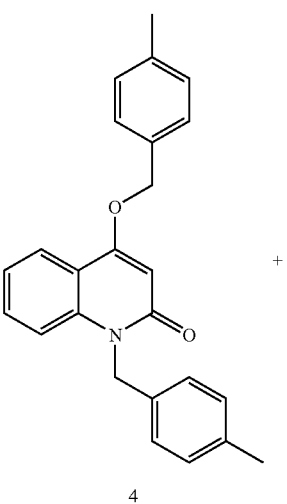

4

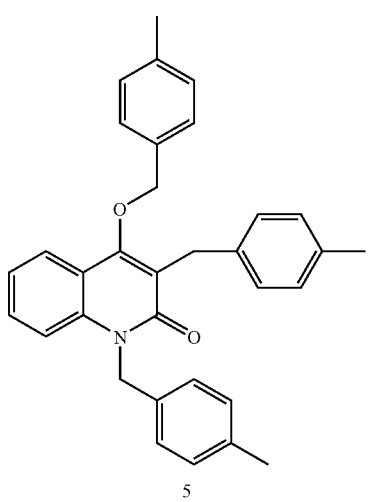

5

To the mixture of 1 (50 mg, 0.31 mmol) and K$_2$CO$_3$ (429 mg, 3.1 mmol) in acetone (3 mL), 2 (345 mg, 1.86 mmol) was added slowly. Then the reaction was stirred at 65° C. overnight. After cooled down, and filtered, the solvent was removed, the given residue was purified using PTLC (eluent: EtOAc/Petroleum ether=1:3) to give 3 (61.3 mg, 25.6%), 4 (43.9 mg, 38.3%) and 5 (12.6 mg, 8.6%) as solids.

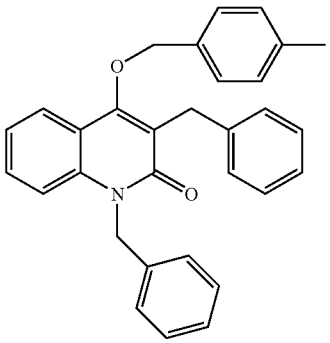

VQ_33645

LC-MS (6.90 min, ES$^+$): calcd: 473.60; Found: 474.48. $^1$H NMR (CDCl$_3$): 7.92 (d, J=8.5 Hz, 1H), 7.165 (t, J=8.5 Hz, 1H), 6.947 (AABB, J=33.5, 8.5 Hz, 4H), 6.931 (AABB, J=49, 8.5 Hz, 4H), 6.922 (t, J=8.5 Hz, 1H), 6.71 (AABB, J=189, 8.5 Hz, 4H), 6.52 (d, J=8.5 Hz, 1H), 5.0 (br, 2H), 3.583 (s, 1H), 3.557 (s, 1H), 3.452 (s, 1H), 3.427 (s, 1H), 2.273 (s, 3H), 2.21 (s, 6H).

Example 5

HCV Replicon Luciferase Assay

Day 0 Cell Seeding and Compound Treatment: Huh-Luc-Neo Cells are seeded at 25,000/well in an opaque-walled 96 plate with Growth Medium (DMEM phenol red free+PS+2 mM glutamine; 100 µl/well). The compounds to be tested are added to the experimental wells (10 µl/well at 10× assay concentration) and the cells are then incubated (5% CO$_2$, 37° C.) for 48 h.

Day 2 Reagent Preparation and Luciferase Assay: The Bright-Glo Luciferase Assay Buffer (Promega) is thawed and equilibrated to room temperature prior to use. The lyophilized Bright-Glo Luciferase Assay Substrate is equilibrated to room temperature prior to use. 10 ml of Bright-Glo Luciferase Assay Buffer is transferred to 1 vial of Bright-Glo Luciferase Assay Substrate bottle and mixed by gently with a Vortex. 100 ul of Bright-Glo Luciferase Assay reagent (Bright-Glo Luciferase Assay Buffer+Bright-Glo Luciferase Assay Substrate Mixture) is added to each well. The well contents are mixed for 5 min. on an orbital shaker at room temperature to induce cell lysis and the luminescence is then measured using a luminometer. The data is analyzed and IC50s are determined using GraphPad Prism 4 software. Hits validated in the Replicon Luciferase assay have IC50s<8.0 µM and show<30% inhibition of Cell Viability at a compound concentration of 100 µM (Cell Titer Glow Assay, cell viability assay conditions identical to HCV Replicon Luciferase Assay conditions).

Example 6

HCV Replicon RNA Assay

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 µl/well). The compounds to be tested are added to the experimental wells (10 µl/well at 10× assay concentration) and the cells are then incubated (5% CO$_2$, 37° C.).

Day 1, Media Change and Compound Treatment: 24 hours after the initial compound treatment the cell culture media is aspirated from the wells and fresh Growth Medium is added (DMEM phenol red free+PS+2 mM glutamine; 100 μl/well). The compounds to be tested are then added to the appropriate experimental wells (10 μl/well at 10 × assay concentration) and the cells are then incubated (5% CO2, 37° C.) for an additional 24 hrs.

Day 2, RNA Isolation and cDNA Synthesis: The cells are washed with 1× Phosphate Buffered Saline (PBS) once. Cells are then lysed and RNA is isolated in 96 well format using a vacuum manifold and the RNAeasy 96 kit (Qiagen) according to the manufacturer's suggested protocol. cDNA is then synthesized from RNA isolated from each well using the Taqman Reverse Transcription Reagents kit (Applied Biosystems) according to manufacturer's suggested protocol.

Day 3, Quantitative PCR Based Measurement of HCV RNA (Taqman Assay): Quantitative PCR analysis to measure HCV RNA expression from cDNA synthesized on Day 2 is performed using the ABI 9700 HT Sequence Detection System (Applied Biosystems) as previously described (Lohman et al, Science 285, 110-113, 1999). The data is analyzed and IC50s are determined using GraphPad Prism 4 software. Hits validated in the Replicon RNA Assay have IC50s<8.0 μM and show <30% inhibition of Cell Viability at a compound concentration of 50 μM (Cell Titer Glow Assay, cell viability assay conditions identical to HCV Replicon RNA Assay conditions).

Example 7

CellTiter-Glo Cell Viability Assay (Promega)

Day 0, Cell Seeding and Compound Treatment: Huh-Luc-Neo Cells are seeded at 25,000/well in an opaque-walled 96 plate with Growth Medium (DMEM phenol red free+PS+2 mM glutamine; 100 ul/well). The compounds to be tested for inhibition of cell viability are added to the experimental wells (10 μl/well at 10× assay concentration) and the cells are then incubated (5% $CO_2$, 37° C.) for 48 h.

Day 2, Reagent Preparation and Assay: The CellTiter-Glo Buffer is thawed and equilibrated to room temperature prior to use. The lyophilized CellTiter-Glo Substrate is equilibrated to room temperature prior to use. 10 ml of CellTiter-Glo Buffer is transferred to 1 vial of CellTiter-Glo Substrate and mixed by gently with a Vortex. 100 μl of CellTiter-Glo Assay reagent (CellTiter-Glo Buffer+CellTiter-Glo Substrate Mixture) is added to each well. The well contents are mixed for 5 min. on an orbital shaker at room temperature to induce cell lysis and the luminescence is then measured using a luminometer.

TABLE 1

| comp. # | Structure | Luciferase IC50 | Toxicity % Inhibition at 100 um (1 dose) | TaqMan IC50 | Toxicity % Inhibition at 50 uM (2 doses) |
|---|---|---|---|---|---|
| VQ_31729 | 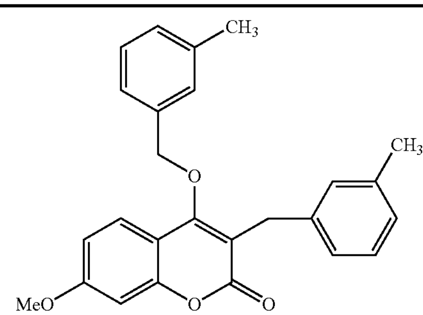 | 3.53 | 3.0 | 0.36 | 5.1 |
| VQ_31734 | 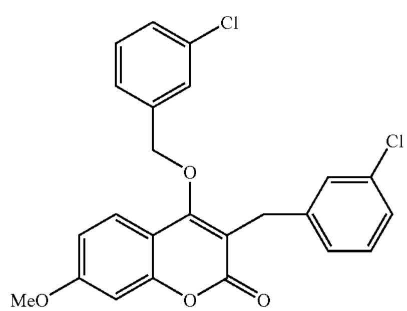 | 3.84 | 4.3 | 0.67 | 0.7 |
| VQ_31711 | 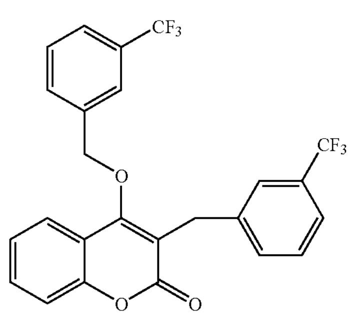 | 5.16 | 4.6 | 0.12 | 4.3 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
| --- | --- | --- | --- | --- | --- |
| VQ_31738 | 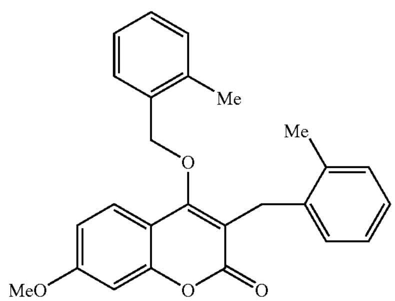 | 5.44 | 23.6 | 0.21 | 6.1 |
| VQ_31748 | 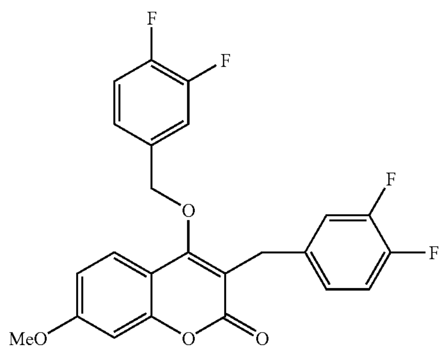 | 5.38 | 10.0 | 1.97 | 4.9 |
| VQ_31754 | 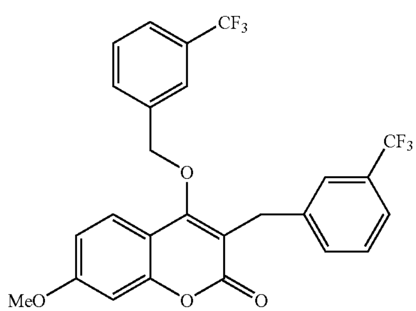 | 5.45 | 2.5 | 5.35 | 1.9 |
| VQ_31758 | 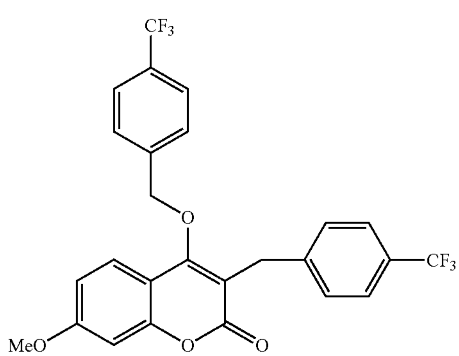 | 6.16 | 14.7 | 5.24 | 2.6 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
| --- | --- | --- | --- | --- | --- |
| VQ_31763 | 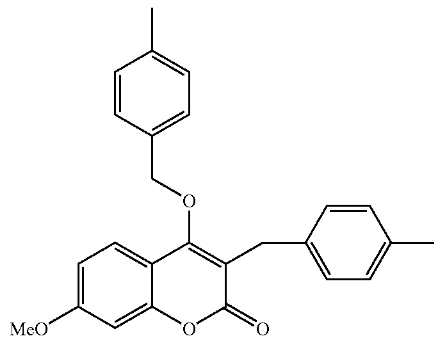 | 8.29 | 4.6 | 0.43 | 6.5 |
| VQ_31712 | 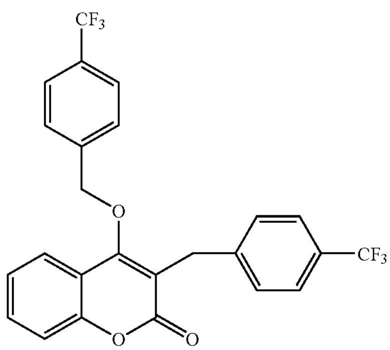 | 4.92 | 16.6 | >30 | 10.0 |
| VQ_31715 | 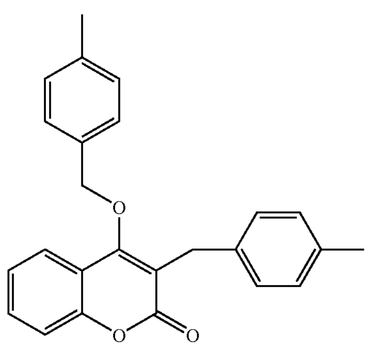 | 2.80 | 53.4 | 0.55 | 13.4 |
| VQ_31744 | 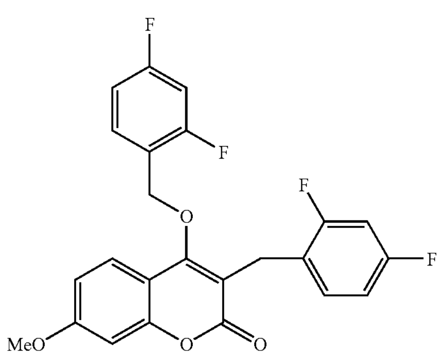 | 4.50 | 10.9 | 0.28 | 7.0 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
|---|---|---|---|---|---|
| VQ_32806 | 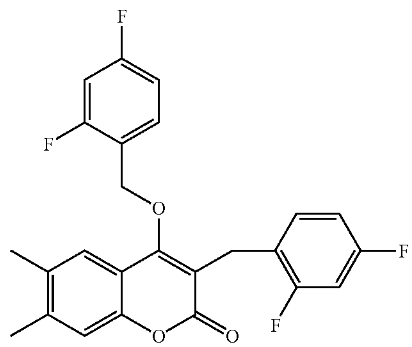 | 5.57 | 16.5 | 1.40 | 8.3 |
| VQ_36312 | 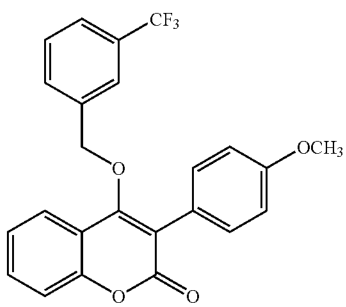 | 3.06 | 5.0 | 0.89 | 40.8 |
| VQ_36341 | 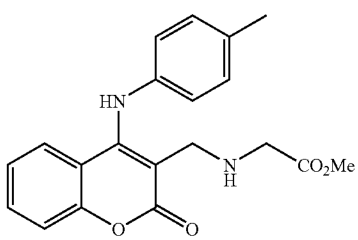 | 0.28 | 14.6 | 0.40 | 31.2 |
| VQ_36343 | 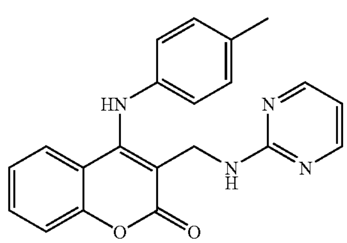 | 0.13 | 21.1 | 0.16 | 37.9 |
| VQ_36467 | 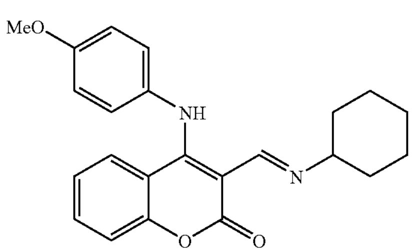 | 51.13 | 22.8 | 0.46 | 13.9 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
| --- | --- | --- | --- | --- | --- |
| VQ_36468 | 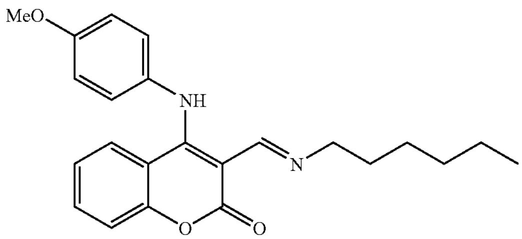 | 43.30 | 40.7 | 0.71 | 16.3 |
| VQ_36469 | 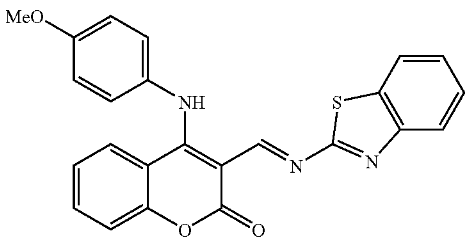 | 53.64 | 14.7 | 4.16 | 3.3 |
| VQ_36470 | 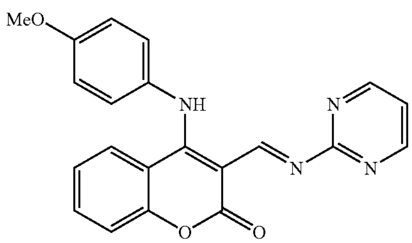 | 59.94 | 12.5 | 4.08 | −2.7 |
| VQ_36471 | 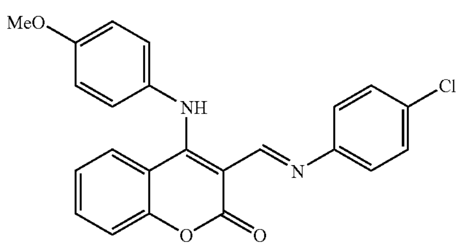 | 0.04 | 9.8 | 1.78 | 15.2 |
| VQ_36472 | 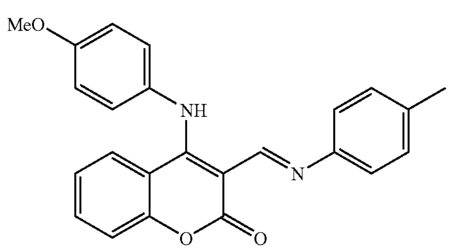 | 0.03 | 5.9 | 0.85 | 6.5 |
| VQ_36473 | 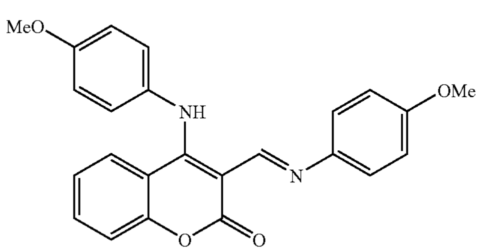 | 0.02 | 4.3 | 1.71 | 10.7 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
| --- | --- | --- | --- | --- | --- |
| VQ_36594 | 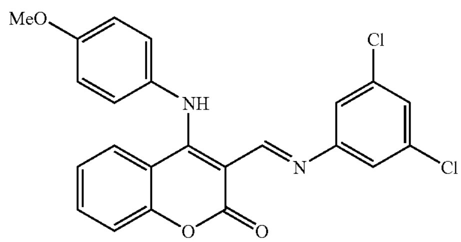 | 0.74 | 9.1 | >30 | 13.7 |
| VQ_32833 | 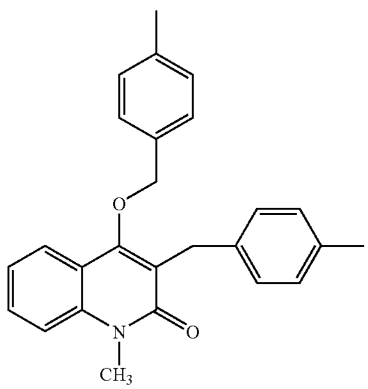 | 2.89 | 34.6 | 0.58 | 20.7 |
| VQ_33645 | 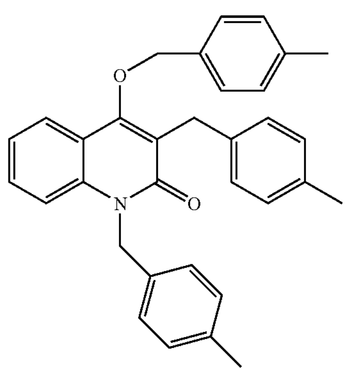 | 2.33 | 21.5 | >30 | 17.2 |
| VQ_34453 | 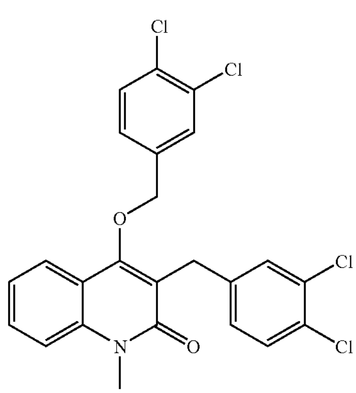 | 8.5 | 24.6 | 1.97 | 12.2 |

TABLE 1-continued

| comp. # | Structure | Luciferase IC50 | Toxicity % Inhibition at 100 um (1 dose) | TaqMan IC50 | Toxicity % Inhibition at 50 uM (2 doses) |
| --- | --- | --- | --- | --- | --- |
| VQ_35027 | 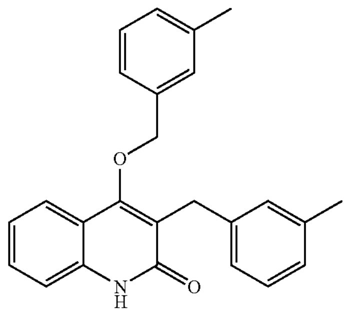 | 2.1 | 4.6 | Inactive | 12.5 |
| VQ_35018 | 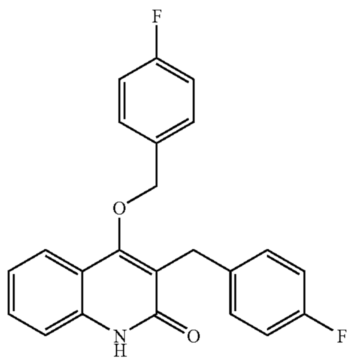 | 1.0 | 10.0 | Inactive | 12.3 |

What is claimed is:

1. A compound having the Formula III:

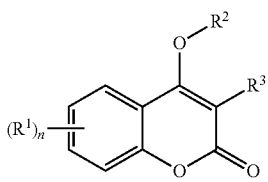

(III)

wherein:

each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO3$R^{11}$, —SO$_2$N($R^{12)(R13}$), -alkyl-O—$R^{11}$, cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5 - or 6- membered ring may contain from 0 to 3 ring heteroatoms and may be further substituted with one or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, and aryl; or $R^{12}$ and $R^{13}$ may be taken together with the nitrogen to which they are attached form a 5 - to 7-membered ring which may optionally contain a further heteroatom, n is 0 to 4;

$R^2$ is selected from the group consisting of aralkyl, aryl;

$R^3$ is selected from the group consisting of aralkyl, aryl, —(CH$_2$)aC(O)$R^{31}$, —(CH$_2$)aC(O)N($R^{32}$)($R^{33}$), (CH$_2$)aC(O)O$R^{31}$, —(CH$_2$)aC(O)N($R^{32}$)($R^{33}$), —(CH$_2$)aN($R^{32}$)($R^{33}$), —CH=N—$R^{34}$, $R^{31}$ selected from aralkyl, and aryl;

$R^{32}$ is selected from H, alkyl, cycloalkyl, cycloalkenyl, alkenyl, alkynyl, aralkyl, and aryl;

$R^{33}$ is selected from aralkyl, and aryl;

$R^{34}$ is selected from aralkyl, and aryl;

a is 0 to 6;

or a pharmaceutically acceptable salt thereof;

with the proviso that R2 is heteroaryl or heteroaralkyl, and/or $R^3$, $R^{31}$, $R^{33}$ and $R^{34}$ are selected from heteroaryl and heteroaralkyl.

2. The compound of claim 1, having the formula IV:

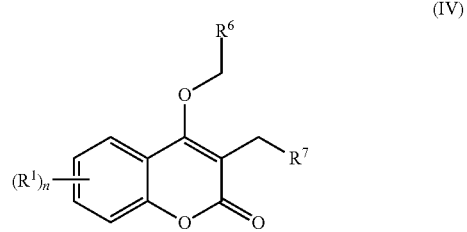

(IV)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO3$R^{11}$, —SO$_2$N($R^{12}$)($R^{13}$), cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, and aryl; or $R^{12}$ and $R^{13}$ may be taken together with the nitrogen to which they are attached form a 5- to 7-membered ring which may optionally contain a further heteroatom,
n is 0 to 4;
$R^6$ is an aryl group;
$R^7$ is selected from the group consisting of aryl, —C(O)$R^{31}$, —C(O)N($R^{32}$)($R^{33}$), —C(O)O$R^{31}$, —C(O)N($R^{32}$)($R^{33}$), —N($R^{32}$)($R^{33}$),
$R^{31}$ selected from aralkyl, and aryl;
$R^{32}$ is selected from H, alkyl, cycloalkyl, cycloalkenyl, alkenyl, alkynyl, aralkyl, and aryl;
$R^{33}$ is selected from aralkyl, and aryl;
or a pharmaceutically acceptable salt thereof;
with the proviso that $R^6$ is heteroaryl or heteroaralkyl, and/or $R^7$, $R^{31}$, and $R^{33}$ are selected from heteroaryl and heteroaralkyl.
3. The compound of claim 2, wherein $R^7$ is an aryl group.
4. The compound of claim 1, having the formula V:

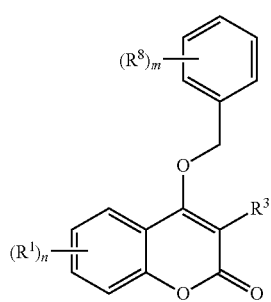

(V)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO3$R^{11}$, —SO$_2$N($R^{12}$)($R^{13}$), -alkyl-O—$R^{11}$, cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^1$;

each $R^{11}$ is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, and aryl; or $R^{12}$ and $R^{13}$ may be taken together with the nitrogen to which they are attached form a 5- to 7-membered ring which may optionally contain a further heteroatom,
n is 0 to 4;
$R^3$ is selected from the group consisting of heteroaralkyl, heteroaryl, —(CH$_2$)aC(O)$R^{31}$, —(CH$_2$)aC(O)N($R^{32}$)($R^{33}$), (CH$_2$)aC(O)O$R^{31}$, —(CH$_2$)aC(O)N($R^{32}$)($R^{33}$), —(CH$_2$)aN($R^{32}$)($R^{33}$), —CH=N—$R^{34}$,
$R^{31}$ is selected from heteroaralkyl, and heteroaryl;
$R^{32}$ is selected from H, alkyl, cycloalkyl, cycloalkenyl, alkenyl, alkynyl, aralkyl, and aryl;
$R^{33}$ is selected from heteroaralkyl, and heteroaryl;
$R^{34}$ is selected from heteroaralkyl, and heteroaryl;
a is 0 to 6;
each $R^8$ is independently selected from the group consisting of halo, alkyl, CN, NO2, CO2$R^{81}$, C(O)$R^{81}$, —O—$R^{81}$, —N($R^{82}$)($R^{83}$), —N($R^{81}$)C(O)$R^{81}$, —N($R^{81}$)SO2$R^{81}$, —S$R^{81}$, C(O)N($R^{82}$)($R^{83}$), —OC(O)$R^{81}$, —OC(O)N($R^{82}$)($R^{83}$), SO2,—SOR $^{81}$, —SO3$R^{81}$, —SO2N($R^{82}$)($R^{83}$), cycloalkyl, cycloalkenyl, and aryl each $R^{81}$ is independently selected from H, alkyl, cycloalkyl, cycloalkenyl, alkenyl, alkynyl, aralkyl, and aryl;
each $R^{82}$ and $R^{83}$ are independently selected from H, alkyl, cycloalkyl, cycloalkenyl, alkenyl, alkynyl, aralkyl, and; or $R^{82}$ and $R^{83}$ may be taken together with the nitrogen to which they are attached form a 5- to 7-membered ring which may optionally contain a further heteroatom; and
m is 0 to 5;
or a pharmaceutically acceptable salt thereof.
5. A compound having the formula VIIa:

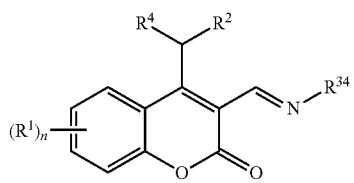

(VII$_a$)

wherein:
each $R^1$ is independently selected from alkyl, alkenyl, alkynyl, aralkyl, —O—$R^{11}$, —N($R^{12}$)($R^{13}$), —N($R^{11}$)C(O)$R^{11}$, —N($R^{11}$)SO$_2R^{11}$, S$R^{11}$, —C(O)$R^{11}$, —C(O)O$R^{11}$, —C(O)N($R^{12}$)($R^{13}$), —OC(O)$R^{11}$, —OC(O)N($R^{12}$)($R^{13}$), CN, CF$_3$, NO$_2$, SO$_2$, —SO$R^{11}$, —SO3$R^{11}$, —SO$_2$N($R^{12}$)($R^{13}$), cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, and aryl; or $R^{12}$ and $R^{13}$ may be taken together with the nitrogen to which they are attached form a 5- to 7-membered ring which may optionally contain a further heteroatom,
n is 0 to 4;
$R^2$ is selected from the group consisting of aralkyl, aryl;
$R^4$ is selected from the group consisting of H, alkyl, cycloalkyl, alkenyl, alkynyl, aralkyl, aryl, —$(CH_2)_bC(O)R^{41}$, —$(CH_2)_bC(O)N(R^{42})(R^{43})$, —$(CH_2)_bC(O)OR^{41}$, and —$(CH2)^bC(O)N(R^{42})(R^{43})$,
each $R^{41}$ is independently selected from H, alkyl, cycloalkyl, cycloalkenyl, alkenyl, alkynyl, aralkyl, and aryl;
$R^{42}$ and $R^{43}$ are independently selected from H, alkyl, cycloalkyl, cycloalkenyl, alkenyl, alkynyl, aralkyl, and aryl;
or $R^{42}$ and $e^{43}$ may be taken together with the nitrogen to which they are attached form a 5- to 7-membered ring which may optionally contain a further heteroatom;
b is 0 to 6;
$R^{34}$ is selected from aralkyl, and aryl;
or a pharmaceutically acceptable salt thereof;
with the proviso that $R^2$ is heteroaryl or heteroaralkyl, and/or $R^{34}$ is selected from heteroaryl, and heteroaralkyl.

6. The compound of claim 5, wherein $R^2$ is an aryl group.
7. The compound of claim 6, wherein $R^4$ is H.
8. A compound having the formula VIII:

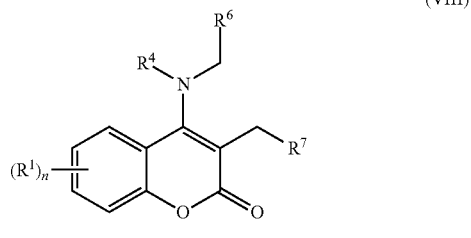

(VIII)

wherein:
each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, $SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO3R^{11}$, —$SO_2N(R^{12})(R^{13})$, -alkyl-O—$R^{11}$, cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^1$;
each is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-alkyl, alkyl-O-aryl, alkenyl, alkynyl, aralkyl, and aryl; or
$R^{12}$ and $R^{13}$ may be taken together with the nitrogen to which they are attached form a 5 - to 7-membered ring which may optionally contain a further heteroatom,
n is 0 to 4;
$R^4$ is selected from the group consisting of H, alkyl, cycloalkyl, alkenyl, alkynyl, aralkyl, aryl, —$(CH_2)_bC(O)R^{41}$, —$(CH_2)_bC(O)N(R^{42})(R^{43})$, —$(CH_2)_bC(O)OR^{41}$, and —$(CH2)bC(O)N(R42)(R43)$,
each $R^{41}$ is independently selected from H, alkyl, cycloalkyl, cycloalkenyl, alkenyl, alkynyl, aralkyl, and aryl;
$R^{42}$ and $R^{43}$ are independently selected from H, alkyl, cycloalkyl, cycloalkenyl, alkenyl, alkynyl, aralkyl, and aryl;
or $R^{42}$ and $e^{43}$ may be taken together with the nitrogen to which they are attached form a 5 - to 7-membered ring which may optionally contain a further heteroatom;
b is 0 to 6;
$R^6$ is an aryl group;
$R^7$ is selected from the group consisting of aryl, —$C(O)R^{31}$, —$C(O)N(R^{32})(R^{33})$, —$C(O)OR^{31}$, —$C(O)N(R^{32})(R^{33})$, —$N(R^{32})(R^{33})$,
$R^{31}$ selected from aralkyl, and aryl;
$R^{32}$ is selected from H, alkyl, cycloalkyl, cycloalkenyl, alkenyl, alkynyl, aralkyl, and aryl;
$R^{33}$ is selected from aralkyl, and aryl;
or a pharmaceutically acceptable salt thereof;
with the proviso that $R^6$ is heteroaryl or heteroaralkyl, and/or $R^7$, $R^{31}$, and $R^{33}$ are selected from heteroaryl and heteroaralkyl.

9. The compound of claim 8, wherein, $R^7$ is an aryl group.
10. A compound having the formula IX:

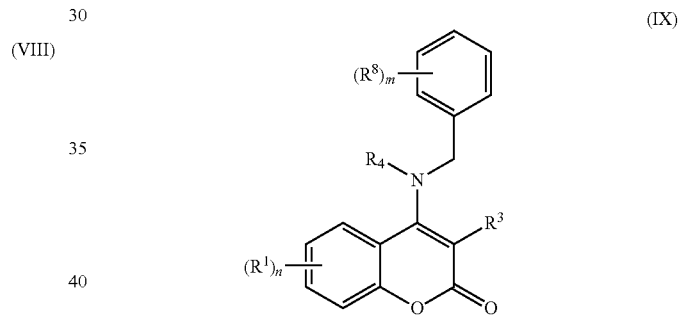

(IX)

wherein:
each $R^1$ is independently selected from alkyl, alkenyl, alkynyl, aralkyl, —O—$R^{11}$, —$N(R^{12})(R^{13})$, —$N(R^{11})C(O)R^{11}$, —$N(R^{11})SO_2R^{11}$, $SR^{11}$, —$C(O)R^{11}$, —$C(O)OR^{11}$, —$C(O)N(R^{12})(R^{13})$, —$OC(O)R^{11}$, —$OC(O)N(R^{12})(R^{13})$, CN, $CF_3$, $NO_2$, $SO_2$, —$SOR^{11}$, —$SO3R^{11}$, —$SO_2N(R^{12})(R^{13})$, -alkyl-O—$R^{11}$, cycloalkyl, cycloalkenyl, halo, phosphate, phosphonate, and aryl; additionally or alternatively two $R^1$ substituents on adjacent ring atoms may be combined to form a fused 5 or 6-membered ring, wherein the fused 5- or 6-membered ring may contain from 0 to 3 ring heteroatoms and may be further substituted with one or more substituents selected from $R^1$;
each $R^{11}$ is independently selected from H, alkyl, alkyl-O-alkyl, alkyl-O-aryl, alkenyl, alkynyl, cycloalkyl, cycloalkenyl, aralkyl, and aryl; each $R^{12}$ and $R^{13}$ are independently selected from H, alkyl, cycloalkyl, cycloalkenyl, alkyl-O-aryl, alkyl-O-aryl, alkenyl, alkynyl, aralkyl, and aryl; or
$R^{12}$ and $R^{13}$ may be taken together with the nitrogen to which they are attached form a 5- to 7-membered ring which may optionally contain a further heteroatom,
n is 0 to 4;

R³ is selected from the group consisting of heteroaralkyl, heteroaryl, —(CH₂)ₐC(O)R³¹, —(CH₂)ₐC(O)N(R³²)(R³³), (CH₂)ₐC(O)OR³¹, —(CH₂)ₐC(O)N(R³²)(R³³), —(CH₂)ₐN(R³²)(R³³), —CH=N—R³⁴, R³¹ selected from heteroaralkyl, and heteroaryl;

R³² is selected from H, alkyl, cycloalkyl, cycloalkenyl, alkenyl, alkynyl, aralkyl, and aryl;

R³³ is selected from heteroaralkyl, and heteroaryl;

R³⁴ is selected from heteroaralkyl, and heteroaryl;

a is 0 to 6;

R⁴ is selected from the group consisting of H, alkyl, cycloalkyl, alkenyl, alkynyl, aralkyl, aryl, —(CH₂)ᵦC(O)R⁴¹, —(CH₂)ᵦC(O)N(R⁴²)(R⁴³), —(CH₂)ᵦC(O)OR⁴¹, and —(CH2)ᵦC(O)N(R42)(R43), each R⁴¹ is independently selected from H, alkyl, cycloalkyl, cycloalkenyl, alkenyl, alkynyl, aralkyl, and aryl;

R⁴² and R⁴³ are independently selected from H, alkyl, cycloalkyl, cycloalkenyl, alkenyl, alkynyl, aralkyl, and aryl;

or R⁴² and e⁴³ may be taken together with the nitrogen to which they are attached form a 5- to 7-membered ring which may optionally contain a further heteroatom;

b is 0 to 6;

each R⁸ is independently selected from the group consisting of halo, alkyl, CN, NO2, CO2R⁸¹, C(O)R⁸¹, —O—R⁸¹,—N(R⁸²)(R⁸³), —N(R⁸¹)C(O)R⁸¹, —N(R⁸¹)SO₂R⁸¹, —SR⁸¹, —C(O)N(R⁸²)(R⁸³), —OC(O)R⁸¹, —OC(O)N(R⁸²)(R⁸³), SO2, —SOR⁸¹, —SO3R⁸¹, —SO₂N(R⁸²)(R⁸³), cycloalkyl, cycloalkenyl, and aryl each R⁸¹ is independently selected from H, alkyl, cycloalkyl, cycloalkenyl, alkenyl, alkynyl, aralkyl, and aryl;

each R⁸² and R⁸³ are independently selected from H, alkyl, cycloalkyl, cycloalkenyl, alkenyl, alkynyl, aralkyl, and;

or R⁸² and R⁸³ may be taken together with the nitrogen to which they are attached form a 5- to 7-membered ring which may optionally contain a further heteroatom; and m is 0 to 5;

or a pharmaceutically acceptable salt thereof.

11. The compound of claim 5, having the formula

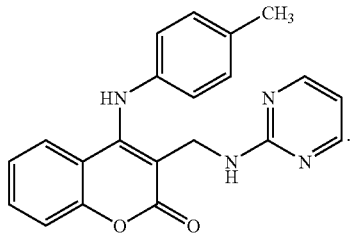

12. The compound of claim 5, having the formula

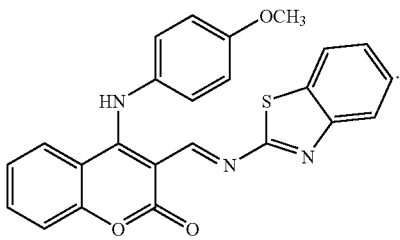

* * * * *

UNITED STATES PATENT AND TRADEMARK OFFICE
CERTIFICATE OF CORRECTION

PATENT NO.        : 8,048,889 B2
APPLICATION NO.   : 11/093846
DATED             : November 1, 2011
INVENTOR(S)       : Bin Xu et al.

Page 1 of 1

It is certified that error appears in the above-identified patent and that said Letters Patent is hereby corrected as shown below:

Column 65, line 7, after "-$SO_2N(R^{12})(R^{13})$," insert -- -alkyl-O-$R^{11}$,--.

Column 66, line 55, after "-$SO_2N(R^{12})(R^{13})$," insert -- -alkyl-O-$R^{11}$,--.

Column 67, line 16, change "$e^{43}$" to "$R^{43}$".

Column 68, line 9, change "$e^{43}$" to "$R^{43}$".

Column 69, line 21, change "$e^{43}$" to "$R^{43}$".

Signed and Sealed this
Sixth Day of March, 2012

David J. Kappos
*Director of the United States Patent and Trademark Office*